(12) United States Patent
Lindahl et al.

(10) Patent No.: US 6,586,580 B1
(45) Date of Patent: *Jul. 1, 2003

(54) PROTEIN RIB, A CELL SURFACE PROTEIN THAT CONFERS IMMUNITY TO MANY STRAINS OF THE GROUP B STREPTOCOCCUS: PROCESS FOR PURIFICATION OF THE PROTEIN, REAGENT KIT AND PHARMACEUTICAL COMPOSITION

(75) Inventors: Gunnar Lindahl, Magnus Stenbocksgatan 5, S-222 24 Lund (SE); Margaretha Stalhammar-Carlemalm, Lund (SE); Lars Stenberg, Lund (SE)

(73) Assignee: Gunnar Lindahl, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,123

(22) Filed: Nov. 5, 1999

Related U.S. Application Data

(62) Division of application No. 08/904,263, filed on Jul. 31, 1997, now Pat. No. 6,015,889, which is a continuation-in-part of application No. 08/487,675, filed on Jun. 7, 1995, now Pat. No. 5,869,064, which is a continuation of application No. PCT/SE94/00246, filed on Mar. 24, 1994.

(30) Foreign Application Priority Data

Mar. 19, 1993 (WO) ............................... PCT/SE93/00234

(51) Int. Cl.[7] ............................................. C07H 21/04
(52) U.S. Cl. ............................ 536/23.5; 514/44; 435/6
(58) Field of Search .......................... 435/6; 536/23.5; 514/44; 530/350; 424/165.1

(56) References Cited

U.S. PATENT DOCUMENTS 4,439,422 A    3/1984  Swenson et al.
5,610,011 A *  3/1997  Smith et al. .................... 435/6
5,648,241 A    7/1997  Michel et al.
5,843,444 A * 12/1998  Michel et al. ............ 424/165.1
5,847,081 A * 12/1998  Michel et al. ............... 530/350
6,015,889 A *  1/2000  Lindahl ...................... 536/23.5

FOREIGN PATENT DOCUMENTS

EP    0367890    5/1990
WO    9104049    4/1991
WO    9217588    10/1992
WO    94/10317  * 5/1994
WO    9421685    9/1994

OTHER PUBLICATIONS

Wastfelt, M et al, Journal of Biological Chemistry, vol. 271(31), pp. 18892–18897, Aug. 2, 1996.*

Michel, JL et al, Proc. Natl. Acad. Sci, vol. 89, pp. 10060–10064, Nov. 1992 (also attached is sequence alignment).*

(List continued on next page.)

Primary Examiner—Lynette R. F. Smith
Assistant Examiner—Ginny Allen Portner
(74) Attorney, Agent, or Firm—Birch, Stewart, Kolasch & Birch, LLP

(57) ABSTRACT

This invention relates to a new protein, designated Rib, and subfragments, multiples or variants thereof, which confers protective immunity against infection with many group B streptococcal strains, in particular those of serotype III. The invention includes a procedure for purification of the protein, a procedure for preparation of highly specific antibodies, a reagent kit, a DNA sequence encoding the protein and a pharmaceutical composition comprising the protein or fragments or variants thereof.

7 Claims, 14 Drawing Sheets

```
676  AATCCTAAGACGCAATCAGACATTGCCAATAAAATAACTGAAGTTACTAATTTAGAAAAAATACTAGTACCTCGA  750
148  N  P  K  T  Q  S  D  I  A  N  K  I  T  E  V  T  N  L  E  K  I  L  V  P  R  172

751  ATCCCA  756               GATGCCGATAAGAATGATCCAGCAGGTAAAGATCAGCAAGTCAATGTA
173  I  P      174   12 repeats: D  A  D  K  N  D  P  A  G  K  D  Q  Q  V  N  V GGTGAGACACCGAAGGCAGAAGATTCTATTGGTAACTTACCAGATCTTCCGAAAGGTACAACAGTAGCCTTTGAA
     G  E  T  P  K  A  E  D  S  I  G  N  L  P  D  L  P  K  G  T  T  V  A  F  E ACTCCAGTTGATACGGCAACACCGGGAGACAAACCAGCAAAAGTTGTTGTGACTTACCCAGATGGTTCAAAAGAT
     T  P  V  D  T  A  T  P  G  D  K  P  A  K  V  V  V  T  Y  P  D  G  S  K  D ACTGTAGATGTGACTGTTAAGGTTGTCGATCCACGTACA              3601  GATGCCGATAAG 3612
     T  V  D  V  T  V  K  V  V  D  P  R  T  partial repeat: 1123  D  A  D  K  1126

3613 AATGATCCAGCAGGTAAAGATCAGCAAGTCAAT 3646 GGTAAAGGAAATAAACTACCAGCAACAGGTGAGAAT 3681
1127 N  D  P  A  G  K  D  Q  Q  V  N  1138 G  K  G  N  K  L  P  A  T  G  E  N  1149

3681 GCAACTCCATTCTTTAATGTTGTAGCTTTGACAATTATGTCATCAGTTGGTTTATTATCTGTTTCTAAGAAAAAA 3756
1150 A  T  P  F  F  N  V  V  A  L  T  I  M  S  S  V  G  L  L  S  V  S  K  K  K  1174

3757 GAGGATTAATCTTTTGACCTAAAATGTCACTAAACTTTTCACCATTTATTGGTGTGAACACATTAATAA      3825
1175 E  D                                                                      1176
```

OTHER PUBLICATIONS

Musser, JM et al, Proceedings of the National Academy of Science of the United States of America, vol. 86(12), pp. 4731–4735, Jun. 1989.*

Wanger, AR et al, Research in veterinary science, vol. 38(2), pp. 202–208, Mar. 1985 (abstract only).*

Blumberg, HM et al, Journal of Infectious Diseases, Sep. 1992, vol. 166(3), pp. 574–579.*

Nagano, Y et al, Journal of Medical microbiology, vol. 35(5), pp. 297–303, Nov. 1991 (abstract only).*

Takahashi, S et al, Journal of Medical Microbiology, vol. 38(3), pp. 191–196, Mar. 1993.*

Forbes, BA et al, Infection Immunity, vol (18)3, pp. 866–867, Dec. 1977 (abstract only).*

Kuypers, JM et al, Infection Immunity, vol. 57(10), pp. 3058–3065, Oct. 1989.*

Jerlstrom, PG et al, Molecular Microbiology, vol. 5(4), pp. 843–849, Apr. 1991 (abstract only).*

Wessels, MR et al, Infection Immunity, vol. 60(2), p. 392–400, Feb. 1992.*

Baker et al., N. Engl. J. Med. 294:753–756 (1976).

Baker, J. Inf. Dis., 161:917–921 (1990).

Pritchard et al., Infect. Immun. 60:1598–1602.

Lewin, Roger, Science, vol. 237, p. 1570, 1987.

Reeck et al. CCell, vol. 50, pp. 667. Aug. 28, 1987.

Carberry–Goh et al., 1987, In:Streptococcal genetics, pp. 22–24.

Michel, James et al, pp. 214–218, In:Genetics and Molecular Biology of Streptococci, Lactococci, and Enterococci, 1991.

Coppel et al., In Methods in Molecular Biology, vol. 21, Antibody Screening of expression Libraries, pp. 277–29.

Modoff et al., Infect & Immun., Jan., p. 204–210, vol. 59(1), 1991.

Baker et al. J. Infect. Dis., Jul., vol. 154(1), p. 47–54, 1986.

Baltimore, R.S. et al., J. of Immun., vol. 118(2), p. 673–678, 1977.

Ferrieri, P., Reviews of Infect. Diseases, vol. 10, Supp. 2, Jul.–Aug., p. S363–S366, 1988.

Russell–Jones, G. J. et al., J. Exp. Med, Nov., vol. 160, p. 1467–1475, 1984.

Salasia, S.I.O. et al., APMIS, vol. 102, p. 925–930, 1994.

Wagner, A. R. et al., Infect. & Immun, May, vol. 55(5), p. 1170–1175, 1987.

Linden, ACTA path. Microbiol. Immun. Scand. Sect. B, 91, p. 145–151, 1983.

Lancefield, R. C. et al., J. of Exp. Med., vol. 142, p. 165–179, 1975.

Mukasa, H. et al., Infect & Immun., vol. 7(4), p. 578–585, 1973.

Glores, A. E. et al., Zentralbl. Bakteriol. Microbiol. Hy., vol. 259(2), p. 165–178, Apr. 1985.

Talay, S. R. et al., Molecular Microbiology, vol. 5(7), pp. 1727–1734 (1991). Linden et al.

Sting et al., J. of Chromatography, 161.497, pp. 258–262 (German) (1989).

* cited by examiner

Chromosomal Streptococcal DNA lane
1+8 λEcoRI/HindIII
2   BM110 DNA before CsCl 1μl
4   BM110 DNA after  CsCl 1μl
6   BM110 DNA Sau3AI       1μl λ Rib 3 DNA
(λ Maxi prep Promega)

lane
1  λEcoRI/HindIII
2  λRib 3
3  λRib 3 BamHI
4  λRib 3 SalI
5  λRib 3 PstI

Figure 7A

```
1    AATATTTGTTTTTAAAGCCTATACTTTACTATGTATAGAGCTATACAGAATAAAGTAAAGGAGAATATTATGTTT         75
                                                                      M  F           -54

76   AGAAGGTCTAAAAATAACAGTTATGATACTTTACAGACGAAACAACGGTTTTCAATTAAGAAGTTAAGTTTGGT        150
     R  R  S  K  N  N  S  Y  D  T  L  Q  T  K  Q  R  F  S  I  K  K  F  K  F  G       -29

151  GCAGCTTCTGTACTAATTGGTATTAGTTTTTTAGGAGGTTTTACTCAAGGCAATTTAATATTCTACAGATACT        225
     A  A  S  V  L  I  G  I  S  F  L  G  G  F  T  Q  G  Q  F  N  I  S  T  D  T       -4

226  GTGTTTGCAGCTGAAGTAATTTCAGGAAGTGCTGTTACGTTAAACACAAATGACTAAAAATGTTCAGAATGGT        300
     V  F  A  A  E  V  I  S  G  S  A  V  T  L  N  T  N  M  T  K  N  V  Q  N  G        22

301  AGAGCATATATAGATTTATATGATGTGAAAAATGGGAAAATAGATCCATTACAATTACGTTAAATTCACCT         375
     R  A  Y  I  D  L  Y  D  V  K  N  G  K  I  D  P  L  Q  L  I  T  L  N  S  P        47

376  GATTAAAAGCTCAGTATGTCATTAGGCAAGGCGGCAATTATTCACACAACCTTCTGAATTGACTACTGTTGGT        450
     D  L  K  A  Q  Y  V  I  R  Q  G  G  N  Y  F  T  Q  P  S  E  L  T  T  V  G        72

451  GCAGCTAGTATTAATTATACAGTATTGAAGACAGATGGAAGTCCTCATACGAAGCCTGATGGACAAGTGGATATT     525
     A  A  S  I  N  Y  T  V  L  K  T  D  G  S  P  H  T  K  P  D  G  Q  V  D  I        97

526  ATAAACGTTTCATTGACTATTTACAATTCTTCAGCTTTGAGAGATAAAATAGATGAAGTTAAAAAGAAAGCGGAA     600
     I  N  V  S  L  T  I  Y  N  S  A  L  R  D  K  I  D  E  V  K  K  K  A  E         122

601  GACCCTAAATGGGACGAGGGAAGTCGCGATAAAGTTTTAGATGATATCAAAACAGATATTGATAAT              675
     D  P  K  W  D  E  G  S  R  D  K  V  L  I  S  L  D  D  I  K  T  D  I  D  N      147
```

Figure 7B

```
676   AATCCTAAGACGCAATCAGACATTGCCAATAAATAACTGAAGTTACTAATTTAGAAAAAATACTAGTACCTCGA  750
148   N  P  K  T  Q  S  D  I  A  N  K  I  T  E  V  T  N  L  E  K  I  L  V  P  R    172

751   ATCCCA  756                     GATGCCGATAAGAATGATCCAGCAGGTAAAGATCAGCAAGTCAATGTA
173   I  P    174    12 repeats: ┌─► D  A  D  K  N  D  P  A  G  K  D  Q  Q  V  N  V
                                 │
      GGTGAGACACCGAAGGCAGAAGATTCTATTGGTAACTTACCAGATCTTCCGAAAGGTACAACAGTAGCCTTTGAA
      G  E  T  P  K  A  E  D  S  I  G  N  L  P  D  L  P  K  G  T  T  V  A  F  E ACTCCAGTTGATACGGCAACACCGGGAGACAAACCAGCAAAAGTTGTTGTGACTTACCCAGATGGTTCAAAAGAT
      T  P  V  D  T  A  T  P  G  D  K  P  A  K  V  V  V  T  Y  P  D  G  S  K  D ACTGTAGATGTGACTGTTAAGGTTGTCGATCCACGTACA                        3601  GATGCCGATAAG  3612
      T  V  D  V  T  V  K  V  V  D  P  R  T ─┐ partial repeat: ┌─►  1123  D  A  D  K    1126
                                             │                 │
                                             ▼                 │
3613  AATGATCCAGCAGGTAAAGAGATCAGCAAGTCAAT  3646  GGTAAAGGAAATAAACTACCAGCAACAGGTGAGAAT  3681
1127  N  D  P  A  G  K  D  Q  Q  V  N      1138  G  K  G  N  K  L  P  A  T  G  E  N    1149

3681  GCAACTCCATTCTTTAATGTTGTAGCTTTGACAATTATGTCATCAGTTGGTTTATTATCTGTTTCTAAGAAAAAA  3756
1150  A  T  P  F  F  N  V  V  A  L  T  I  M  S  S  V  G  L  L  S  V  S  K  K  K    1174

3757  GAGGATTAATCTTTTGACCTAAAAATGTCACTAAAACTTTTCACCATTATTGGTGTGAACACATTAATAA  3825
1175  E  D                                                                      1176
```

```
Rib  -55  MFRRSKNNSYDTLQTKQRFSIKKFKFGAASVLIGISFLGGFTQGQFNIST   -6
          |||||||||||||:|||||||||||||||||||:||||.|||.:||.
α    -56  MFRRSKNNSYDTSQTKQRFSIKKFKFGAASVLIGLSFLGGVTQGNLNIFE   -7

-5  DTVFAAEVISGSAVTLNTNMTKNVQNGRAYIDLYDVKNGKIDPLQLITLN   45
          :.:.||..|.|||.|||:|||:||.|||||||||| ||||||||||.|:
      -6  ESIVAASTIPGSAATLNTSITKNIQNGNAYIDLYDVKLGKIDPLQLIVLE   44

46  SPDLKAQYVIRQGGNYFTQPSELTTVGAASINYTVLKTDGSPHTKPDGQV   95
          .:.:|.||:|||..|:::.|:|  ..| ||:|.::.||  |.|.|||:
      45  .QGFTAKYVFRQGTKYYGDVSQLQSTGRASLTYNIFGEDGLPHVKTDGQI   93

96  DIINVSLTIYNSSALRDKIDEVKKKAEDPKWDEGSRDKVLISLDDIKTDI  145
          ||:.|||||:|..||||:||:...:|||||:|||..||.:|.|||||
      94  DIVSVALTIYDSTTLRDKIEEVRTNANDPKWTEESRTEVLTGLDTIKTDI  143

146  DNNPKTQSDIANKITEVTNLEKILVPRIP                      174
          |||||||.|..:||.||.::|||.|
     144  DNNPKTQTDIDSKIVEVNELEKLLVLS..                      170
```

12 or 9 repeats
```
175  ..DADKNDPAGKDQQVNVGETPKAEDSIGNL...PDLPKGTTVAFETPVD
     || || ||.|  :   |  |  .:...|.:|  |. |.||.||..:|
171  VPDKDKYDPTGGETTVPQG.TPVSDKEITDLVKIPDGSKGVPTVVGDRPD
                                                              partial repeat
     TATPGDKPAKVVVTYPDGSKDTVDVTVKVVDPRT DADKNDPAGKDQQVN    1137
     |..|||...| |||||.|||:|||.||||....  |||||||||||||
     TNVPGDHKVTVEVTYPDGTKDTVEVTVHVTPKP  VPDKDKYDPTG          919

1138  GKGNKLPATGENATPFFNVVALTIMSSVGLLSVSKKKED          1176
          |||||||||||||||||||.|||:|||||||||||||||
     920  KAQQVNGKGNKLPATGENATPFFNVAALTIISSVGLLSVSKKKED      964
```

FIG.9A

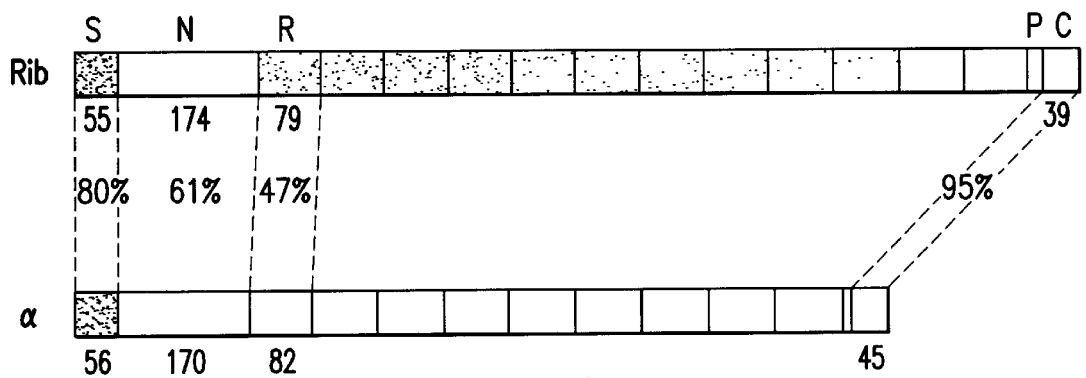

FIG.9B

SEQUENCE LISTING

<160> NUMBER OF SEQ ID NOS: 9

<210> SEQ ID NO 1
<211> LENGTH: 12
<212> TYPE: PRT
<213> ORGANISM: Group B Streptococcus - Strain BS30, type III

```
<400> SEQUENCE: 1

Ala Glu Val Ile Ser Gly Asp Ala Val Thr Leu Asn
1               5                  10

<210> SEQ ID NO 2
<211> LENGTH: 12
<212> TYPE: PRT
<213> ORGANISM: Group B Streptococcus - Strain BM110

<400> SEQUENCE: 2

Ala Glu Val Ile Ser Gly Ser Ala Val Thr Leu Asn
1               5                  10

<210> SEQ ID NO 3
<211> LENGTH: 3825
<212> TYPE: DNA
<213> ORGANISM: Group B Streptococcus - Strain BM110
<220> FEATURE:
<221> NAME/KEY: CDS
<222> LOCATION: (70)..(3762)
<223> OTHER INFORMATION:

<400> SEQUENCE: 3
aatatttgtt tttaaagcct atactttact atgtatagag ctatacagaa taaagtaaag      60 gagaatatt atg ttt aga agg tct aaa aat aac agt tat gat act tta cag    111
           Met Phe Arg Arg Ser Lys Asn Asn Ser Tyr Asp Thr Leu Gln
               1               5                  10 acg aaa caa cgg ttt tca att aag aag ttt aag ttt ggt gca gct tct      159
Thr Lys Gln Arg Phe Ser Ile Lys Lys Phe Lys Phe Gly Ala Ala Ser
 15              20                  25                  30 gta cta att ggt att agt ttt tta gga ggt ttt act caa ggg caa ttt      207
Val Leu Ile Gly Ile Ser Phe Leu Gly Gly Phe Thr Gln Gly Gln Phe
                 35                  40                  45 aat att tct aca gat act gtg ttt gca gct gaa gta att tca gga agt      255
Asn Ile Ser Thr Asp Thr Val Phe Ala Ala Glu Val Ile Ser Gly Ser
             50                  55                  60 gct gtt acg tta aac aca aat atg act aaa aat gtt cag aat ggt aga      303
Ala Val Thr Leu Asn Thr Asn Met Thr Lys Asn Val Gln Asn Gly Arg
         65                  70                  75 gca tat ata gat tta tat gat gtg aaa aat ggg aaa ata gat cca tta      351
Ala Tyr Ile Asp Leu Tyr Asp Val Lys Asn Gly Lys Ile Asp Pro Leu
     80                  85                  90 caa tta att acg tta aat tca cct gat tta aaa gct cag tat gtc att      399
Gln Leu Ile Thr Leu Asn Ser Pro Asp Leu Lys Ala Gln Tyr Val Ile
 95                 100                 105                 110 agg caa ggc ggc aat tat ttc aca caa cct tct gaa ttg act act gtt      447
Arg Gln Gly Gly Asn Tyr Phe Thr Gln Pro Ser Glu Leu Thr Thr Val
                115                 120                 125 ggt gca gct agt att aat tat aca gta ttg aag aca gat gga agt cct      495
Gly Ala Ala Ser Ile Asn Tyr Thr Val Leu Lys Thr Asp Gly Ser Pro
            130                 135                 140 cat acg aag cct gat gga caa gtg gat att ata aac gtt tca ttg act      543
His Thr Lys Pro Asp Gly Gln Val Asp Ile Ile Asn Val Ser Leu Thr
        145                 150                 155 att tac aat tct tca gct ttg aga gat aaa ata gat gaa gtt aaa aag      591
Ile Tyr Asn Ser Ser Ala Leu Arg Asp Lys Ile Asp Glu Val Lys Lys
    160                 165                 170 aaa gcg gaa gac cct aaa tgg gac gag gga agt cgc gat aaa gtt ttg      639
Lys Ala Glu Asp Pro Lys Trp Asp Glu Gly Ser Arg Asp Lys Val Leu
175                 180                 185                 190
```

```
ata agt tta gat gat atc aaa aca gat att gat aat aat cct aag acg     687
Ile Ser Leu Asp Asp Ile Lys Thr Asp Ile Asp Asn Asn Pro Lys Thr
            195                 200                 205 caa tca gac att gcc aat aaa ata act gaa gtt act aat tta gaa aaa     735
Gln Ser Asp Ile Ala Asn Lys Ile Thr Glu Val Thr Asn Leu Glu Lys
        210                 215                 220 ata cta gta cct cga atc cca gat gcc gat aag aat gat cca gca ggt     783
Ile Leu Val Pro Arg Ile Pro Asp Ala Asp Lys Asn Asp Pro Ala Gly
                225                 230                 235 aaa gat cag caa gtc aat gta ggt gag aca ccg aag gca gaa gat tct     831
Lys Asp Gln Gln Val Asn Val Gly Glu Thr Pro Lys Ala Glu Asp Ser
    240                 245                 250 att ggt aac tta cca gat ctt ccg aaa ggt aca aca gta gcc ttt gaa     879
Ile Gly Asn Leu Pro Asp Leu Pro Lys Gly Thr Thr Val Ala Phe Glu
255                 260                 265                 270 act cca gtt gat acg gca aca ccg gga gac aaa cca gca aaa gtt gtt     927
Thr Pro Val Asp Thr Ala Thr Pro Gly Asp Lys Pro Ala Lys Val Val
                275                 280                 285 gtg act tac cca gat ggt tca aaa gat act gta gat gtg act gtt aag     975
Val Thr Tyr Pro Asp Gly Ser Lys Asp Thr Val Asp Val Thr Val Lys
            290                 295                 300 gtt gtc gat cca cgt aca gat gcc gat aag aat gat cca gca ggt aaa    1023
Val Val Asp Pro Arg Thr Asp Ala Asp Lys Asn Asp Pro Ala Gly Lys
        305                 310                 315 gat cag caa gtc aat gta ggt gag aca ccg aag gca gaa gat tct att    1071
Asp Gln Gln Val Asn Val Gly Glu Thr Pro Lys Ala Glu Asp Ser Ile
    320                 325                 330 ggt aac tta cca gat ctt ccg aaa ggt aca aca gta gcc ttt gaa act    1119
Gly Asn Leu Pro Asp Leu Pro Lys Gly Thr Thr Val Ala Phe Glu Thr
335                 340                 345                 350 cca gtt gat acg gca aca ccg gga gac aaa cca gca aaa gtt gtt gtg    1167
Pro Val Asp Thr Ala Thr Pro Gly Asp Lys Pro Ala Lys Val Val Val
                355                 360                 365 act tac cca gat ggt tca aaa gat act gta gat gtg act gtt aag gtt    1215
Thr Tyr Pro Asp Gly Ser Lys Asp Thr Val Asp Val Thr Val Lys Val
            370                 375                 380 gtc gat ccg cgt aca gat gcc gat aag aat gat cca gca ggt aaa gat    1263
Val Asp Pro Arg Thr Asp Ala Asp Lys Asn Asp Pro Ala Gly Lys Asp
        385                 390                 395 cag caa gtc aat gta ggt gag aca ccg aag gca gaa gat tct att ggt    1311
Gln Gln Val Asn Val Gly Glu Thr Pro Lys Ala Glu Asp Ser Ile Gly
    400                 405                 410 aac tta cca gat ctt ccg aaa ggt aca aca gta gcc ttt gaa act cca    1359
Asn Leu Pro Asp Leu Pro Lys Gly Thr Thr Val Ala Phe Glu Thr Pro
415                 420                 425                 430 gtt gat acg gca aca ccg gga gac aaa cca gca aaa gtt gtt gtg act    1407
Val Asp Thr Ala Thr Pro Gly Asp Lys Pro Ala Lys Val Val Val Thr
                435                 440                 445 tac cca gat ggt tca aaa gat act gta gat gtg act gtt aag gtt gtc    1455
Tyr Pro Asp Gly Ser Lys Asp Thr Val Asp Val Thr Val Lys Val Val
            450                 455                 460 gat ccg cgt aca gat gcc gat aag aat gat cca gca ggt aaa gat cag    1503
Asp Pro Arg Thr Asp Ala Asp Lys Asn Asp Pro Ala Gly Lys Asp Gln
        465                 470                 475 caa gtc aat gta ggt gag aca ccg aag gca gaa gat tct att ggt aac    1551
Gln Val Asn Val Gly Glu Thr Pro Lys Ala Glu Asp Ser Ile Gly Asn
    480                 485                 490 tta cca gat ctt ccg aaa ggt aca aca gta gcc ttt gaa act cca gtt    1599
Leu Pro Asp Leu Pro Lys Gly Thr Thr Val Ala Phe Glu Thr Pro Val
495                 500                 505                 510
```

```
gat acg gca aca ccg gga gac aaa cca gca aaa gtt gtt gtg act tac    1647
Asp Thr Ala Thr Pro Gly Asp Lys Pro Ala Lys Val Val Val Thr Tyr
            515                 520                 525 cca gat ggt tca aaa gat act gta gat gtg act gtt aag gtt gtc gat    1695
Pro Asp Gly Ser Lys Asp Thr Val Asp Val Thr Val Lys Val Val Asp
            530                 535                 540 ccg cgt aca gat gcc gat aag aat gat cca gca ggt aaa gat cag caa    1743
Pro Arg Thr Asp Ala Asp Lys Asn Asp Pro Ala Gly Lys Asp Gln Gln
            545                 550                 555 gtc aat gta ggt gag aca ccg aag gca gaa gat tct att ggt aac tta    1791
Val Asn Val Gly Glu Thr Pro Lys Ala Glu Asp Ser Ile Gly Asn Leu
            560                 565                 570 cca gat ctt ccg aaa ggt aca aca gta gcc ttt gaa act cca gtt gat    1839
Pro Asp Leu Pro Lys Gly Thr Thr Val Ala Phe Glu Thr Pro Val Asp
575                 580                 585                 590 acg gca aca ccg gga gac aaa cca gca aaa gtt gtt gtg act tac cca    1887
Thr Ala Thr Pro Gly Asp Lys Pro Ala Lys Val Val Val Thr Tyr Pro
                595                 600                 605 gat ggt tca aaa gat act gta gat gtg act gtt aag gtt gtc gat ccg    1935
Asp Gly Ser Lys Asp Thr Val Asp Val Thr Val Lys Val Val Asp Pro
                610                 615                 620 cgt aca gat gcc gat aag aat gat cca gca ggt aaa gat cag caa gtc    1983
Arg Thr Asp Ala Asp Lys Asn Asp Pro Ala Gly Lys Asp Gln Gln Val
                625                 630                 635 aat gta ggt gag aca ccg aag gca gaa gat tct att ggt aac tta cca    2031
Asn Val Gly Glu Thr Pro Lys Ala Glu Asp Ser Ile Gly Asn Leu Pro
            640                 645                 650 gat ctt ccg aaa ggt aca aca gta gcc ttt gaa act cca gtt gat acg    2079
Asp Leu Pro Lys Gly Thr Thr Val Ala Phe Glu Thr Pro Val Asp Thr
655                 660                 665                 670 gca aca ccg gga gac aaa cca gca aaa gtt gtt gtg act tac cca gat    2127
Ala Thr Pro Gly Asp Lys Pro Ala Lys Val Val Val Thr Tyr Pro Asp
                675                 680                 685 ggt tca aaa gat act gta gat gtg act gtt aag gtt gtc gat ccg cgt    2175
Gly Ser Lys Asp Thr Val Asp Val Thr Val Lys Val Val Asp Pro Arg
                690                 695                 700 aca gat gcc gat aag aat gat cca gca ggt aaa gat cag caa gtc aat    2223
Thr Asp Ala Asp Lys Asn Asp Pro Ala Gly Lys Asp Gln Gln Val Asn
            705                 710                 715 gta ggt gag aca ccg aag gca gaa gat tct att ggt aac tta cca gat    2271
Val Gly Glu Thr Pro Lys Ala Glu Asp Ser Ile Gly Asn Leu Pro Asp
720                 725                 730 ctt ccg aaa ggt aca aca gta gcc ttt gaa act cca gtt gat acg gca    2319
Leu Pro Lys Gly Thr Thr Val Ala Phe Glu Thr Pro Val Asp Thr Ala
735                 740                 745                 750 aca ccg gga gac aaa cca gca aaa gtt gtt gtg act tac cca gat ggt    2367
Thr Pro Gly Asp Lys Pro Ala Lys Val Val Val Thr Tyr Pro Asp Gly
                755                 760                 765 tca aaa gat act gta gat gtg act gtt aag gtt gtc gat ccg cgt aca    2415
Ser Lys Asp Thr Val Asp Val Thr Val Lys Val Val Asp Pro Arg Thr
            770                 775                 780 gat gcc gat aag aat gat cca gca ggt aaa gat cag caa gtc aat gta    2463
Asp Ala Asp Lys Asn Asp Pro Ala Gly Lys Asp Gln Gln Val Asn Val
            785                 790                 795 ggt gag aca ccg aag gca gaa gat tct att ggt aac tta cca gat ctt    2511
Gly Glu Thr Pro Lys Ala Glu Asp Ser Ile Gly Asn Leu Pro Asp Leu
        800                 805                 810 ccg aaa ggt aca aca gta gcc ttt gaa act cca gtt gat acg gca aca    2559
Pro Lys Gly Thr Thr Val Ala Phe Glu Thr Pro Val Asp Thr Ala Thr
```

|     |     |     |     |     |     |     |     |     |     |     |     |     |     |     |      |
| --- | --- | --- | --- | --- | --- | --- | --- | --- | --- | --- | --- | --- | --- | --- | ---- |
| 815 |     |     |     |     | 820 |     |     |     |     | 825 |     |     |     |     | 830  |
| ccg | gga | gac | aaa | cca | gca | aaa | gtt | gtt | gtg | act | tac | cca | gat | ggt | tca  | 2607 |
| Pro | Gly | Asp | Lys | Pro | Ala | Lys | Val | Val | Val | Thr | Tyr | Pro | Asp | Gly | Ser  |
|     |     |     |     | 835 |     |     |     |     | 840 |     |     |     |     | 845 |      |
| aaa | gat | act | gta | gat | gtg | act | gtt | aag | gtt | gtc | gat | ccg | cgt | aca | gat  | 2655 |
| Lys | Asp | Thr | Val | Asp | Val | Thr | Val | Lys | Val | Val | Asp | Pro | Arg | Thr | Asp  |
|     |     |     | 850 |     |     |     |     | 855 |     |     |     |     | 860 |     |      |
| gcc | gat | aag | aat | gat | cca | gca | ggt | aaa | gat | cag | caa | gtc | aat | gta | ggt  | 2703 |
| Ala | Asp | Lys | Asn | Asp | Pro | Ala | Gly | Lys | Asp | Gln | Gln | Val | Asn | Val | Gly  |
|     |     | 865 |     |     |     |     | 870 |     |     |     |     | 875 |     |     |      |
| gag | aca | ccg | aag | gca | gaa | gat | tct | att | ggt | aac | tta | cca | gat | ctt | ccg  | 2751 |
| Glu | Thr | Pro | Lys | Ala | Glu | Asp | Ser | Ile | Gly | Asn | Leu | Pro | Asp | Leu | Pro  |
|     | 880 |     |     |     |     | 885 |     |     |     |     | 890 |     |     |     |      |
| aaa | ggt | aca | aca | gta | gcc | ttt | gaa | act | cca | gtt | gat | acg | gca | aca | ccg  | 2799 |
| Lys | Gly | Thr | Thr | Val | Ala | Phe | Glu | Thr | Pro | Val | Asp | Thr | Ala | Thr | Pro  |
| 895 |     |     |     |     | 900 |     |     |     |     | 905 |     |     |     |     | 910  |
| gga | gac | aaa | cca | gca | aaa | gtt | gtt | gtg | act | tac | cca | gat | ggt | tca | aaa  | 2847 |
| Gly | Asp | Lys | Pro | Ala | Lys | Val | Val | Val | Thr | Tyr | Pro | Asp | Gly | Ser | Lys  |
|     |     |     |     | 915 |     |     |     |     | 920 |     |     |     |     | 925 |      |
| gat | act | gta | gat | gtg | act | gtt | aag | gtt | gtc | gat | ccg | cgt | aca | gat | gcc  | 2895 |
| Asp | Thr | Val | Asp | Val | Thr | Val | Lys | Val | Val | Asp | Pro | Arg | Thr | Asp | Ala  |
|     |     |     | 930 |     |     |     |     | 935 |     |     |     |     | 940 |     |      |
| gat | aag | aat | gat | cca | gca | ggt | aaa | gat | cag | caa | gtc | aat | gta | ggt | gag  | 2943 |
| Asp | Lys | Asn | Asp | Pro | Ala | Gly | Lys | Asp | Gln | Gln | Val | Asn | Val | Gly | Glu  |
|     |     | 945 |     |     |     |     | 950 |     |     |     |     | 955 |     |     |      |
| aca | ccg | aag | gca | gaa | gat | tct | att | ggt | aac | tta | cca | gat | ctt | ccg | aaa  | 2991 |
| Thr | Pro | Lys | Ala | Glu | Asp | Ser | Ile | Gly | Asn | Leu | Pro | Asp | Leu | Pro | Lys  |
|     | 960 |     |     |     |     | 965 |     |     |     |     | 970 |     |     |     |      |
| ggt | aca | aca | gta | gcc | ttt | gaa | act | cca | gtt | gat | acg | gca | aca | ccg | gga  | 3039 |
| Gly | Thr | Thr | Val | Ala | Phe | Glu | Thr | Pro | Val | Asp | Thr | Ala | Thr | Pro | Gly  |
| 975 |     |     |     |     | 980 |     |     |     |     | 985 |     |     |     |     | 990  |
| gac | aaa | cca | gca | aaa | gtt | gtt | gtg | act | tac | cca | gat | ggt | tca | aaa | gat  | 3087 |
| Asp | Lys | Pro | Ala | Lys | Val | Val | Val | Thr | Tyr | Pro | Asp | Gly | Ser | Lys | Asp  |
|     |     |     | 995 |     |     |     | 1000|     |     |     |     | 1005|     |     |      |
| act | gta | gat | gtg | act | gtt | aag | gtt | gtc | gat | ccg | cgt | aca | gat | gcc |      | 3132 |
| Thr | Val | Asp | Val | Thr | Val | Lys | Val | Val | Asp | Pro | Arg | Thr | Asp | Ala |      |
|     |     |     | 1010|     |     |     |     | 1015|     |     |     | 1020|     |     |      |
| gat | aag | aat | gat | cca | gca | ggt | aaa | gat | cag | caa | gtc | aat | gta | ggt |      | 3177 |
| Asp | Lys | Asn | Asp | Pro | Ala | Gly | Lys | Asp | Gln | Gln | Val | Asn | Val | Gly |      |
|     |     | 1025|     |     |     |     | 1030|     |     |     |     | 1035|     |     |      |
| gag | aca | ccg | aag | gca | gaa | gat | tct | att | ggt | aac | tta | cca | gat | ctt |      | 3222 |
| Glu | Thr | Pro | Lys | Ala | Glu | Asp | Ser | Ile | Gly | Asn | Leu | Pro | Asp | Leu |      |
|     | 1040|     |     |     |     | 1045|     |     |     |     | 1050|     |     |     |      |
| ccg | aaa | ggt | aca | aca | gta | gcc | ttt | gaa | act | cca | gtt | gat | acg | gca |      | 3267 |
| Pro | Lys | Gly | Thr | Thr | Val | Ala | Phe | Glu | Thr | Pro | Val | Asp | Thr | Ala |      |
|     | 1055|     |     |     |     | 1060|     |     |     |     | 1065|     |     |     |      |
| aca | ccg | gga | gac | aaa | cca | gca | aaa | gtt | gtt | gtg | act | tac | cca | gat |      | 3312 |
| Thr | Pro | Gly | Asp | Lys | Pro | Ala | Lys | Val | Val | Val | Thr | Tyr | Pro | Asp |      |
|     | 1070|     |     |     |     | 1075|     |     |     |     | 1080|     |     |     |      |
| ggt | tca | aaa | gat | act | gta | gat | gtg | act | gtt | aag | gtt | gtc | gat | ccg |      | 3357 |
| Gly | Ser | Lys | Asp | Thr | Val | Asp | Val | Thr | Val | Lys | Val | Val | Asp | Pro |      |
|     | 1085|     |     |     |     | 1090|     |     |     |     | 1095|     |     |     |      |
| cgt | aca | gat | gcc | gat | aag | aat | gat | cca | gca | ggt | aaa | gat | cag | caa |      | 3402 |
| Arg | Thr | Asp | Ala | Asp | Lys | Asn | Asp | Pro | Ala | Gly | Lys | Asp | Gln | Gln |      |
|     | 1100|     |     |     |     | 1105|     |     |     |     | 1110|     |     |     |      |
| gtc | aat | gta | ggt | gag | aca | ccg | aag | gca | gaa | gat | tct | att | ggt | aac |      | 3447 |
| Val | Asn | Val | Gly | Glu | Thr | Pro | Lys | Ala | Glu | Asp | Ser | Ile | Gly | Asn |      |
|     | 1115|     |     |     |     | 1120|     |     |     |     | 1125|     |     |     |      |
| tta | cca | gat | ctt | ccg | aaa | ggt | aca | aca | gta | gcc | ttt | gaa | act | cca |      | 3492 |

-continued

```
Leu Pro Asp Leu  Pro Lys Gly Thr Thr  Val Ala Phe Glu Thr  Pro
            1130                 1135                 1140 gtt gat acg gca  aca ccg gga gac aaa  cca gca aaa gtt gtt  gtg      3537
Val Asp Thr Ala  Thr Pro Gly Asp Lys  Pro Ala Lys Val Val  Val
            1145                 1150                 1155 act tac cca gat  ggt tca aaa gat act  gta gat gtg act gtt  aag      3582
Thr Tyr Pro Asp  Gly Ser Lys Asp Thr  Val Asp Val Thr Val  Lys
            1160                 1165                 1170 gtt gtc gat ccg  cgt aca gat gcc gat  aag aat gat cca gca  ggt      3627
Val Val Asp Pro  Arg Thr Asp Ala Asp  Lys Asn Asp Pro Ala  Gly
            1175                 1180                 1185 aaa gat cag caa  gtc aat ggt aaa gga  aat aaa cta cca gca  aca      3672
Lys Asp Gln Gln  Val Asn Gly Lys Gly  Asn Lys Leu Pro Ala  Thr
            1190                 1195                 1200 ggt gag aat gca  act cca ttc ttt aat  gtt gta gct ttg aca  att      3717
Gly Glu Asn Ala  Thr Pro Phe Phe Asn  Val Val Ala Leu Thr  Ile
            1205                 1210                 1215 atg tca tca gtt  ggt tta tta tct gtt  tct aag aaa aaa gag  gat      3762
Met Ser Ser Val  Gly Leu Leu Ser Val  Ser Lys Lys Lys Glu  Asp
            1220                 1225                 1230 taatcttttg acctaaaatg tcactaaact tttcaccatt tattggtgtg aacacattaa   3822
taa                                                                 3825

<210> SEQ ID NO 4
<211> LENGTH: 1231
<212> TYPE: PRT
<213> ORGANISM: Group B Streptococcus - Strain BM110

<400> SEQUENCE: 4

Met Phe Arg Arg Ser Lys Asn Asn Ser Tyr Asp Thr Leu Gln Thr Lys
1               5                   10                  15

Gln Arg Phe Ser Ile Lys Lys Phe Lys Phe Gly Ala Ala Ser Val Leu
            20                  25                  30

Ile Gly Ile Ser Phe Leu Gly Gly Phe Thr Gln Gly Gln Phe Asn Ile
        35                  40                  45

Ser Thr Asp Thr Val Phe Ala Ala Glu Val Ile Ser Gly Ser Ala Val
    50                  55                  60

Thr Leu Asn Thr Asn Met Thr Lys Asn Val Gln Asn Gly Arg Ala Tyr
65                  70                  75                  80

Ile Asp Leu Tyr Asp Val Lys Asn Gly Lys Ile Asp Pro Leu Gln Leu
                85                  90                  95

Ile Thr Leu Asn Ser Pro Asp Leu Lys Ala Gln Tyr Val Ile Arg Gln
            100                 105                 110

Gly Gly Asn Tyr Phe Thr Gln Pro Ser Glu Leu Thr Thr Val Gly Ala
        115                 120                 125

Ala Ser Ile Asn Tyr Thr Val Leu Lys Thr Asp Gly Ser Pro His Thr
    130                 135                 140

Lys Pro Asp Gly Gln Val Asp Ile Ile Asn Val Ser Leu Thr Ile Tyr
145                 150                 155                 160

Asn Ser Ser Ala Leu Arg Asp Lys Ile Asp Glu Val Lys Lys Lys Ala
                165                 170                 175

Glu Asp Pro Lys Trp Asp Glu Gly Ser Arg Asp Lys Val Leu Ile Ser
            180                 185                 190

Leu Asp Asp Ile Lys Thr Asp Ile Asp Asn Asn Pro Lys Thr Gln Ser
        195                 200                 205

Asp Ile Ala Asn Lys Ile Thr Glu Val Thr Asn Leu Glu Lys Ile Leu
```

```
                210                 215                 220
Val Pro Arg Ile Pro Asp Ala Asp Lys Asn Asp Pro Ala Gly Lys Asp
225                 230                 235                 240

Gln Gln Val Asn Val Gly Glu Thr Pro Lys Ala Glu Asp Ser Ile Gly
                245                 250                 255

Asn Leu Pro Asp Leu Pro Lys Gly Thr Thr Val Ala Phe Glu Thr Pro
                260                 265                 270

Val Asp Thr Ala Thr Pro Gly Asp Lys Pro Ala Lys Val Val Val Thr
                275                 280                 285

Tyr Pro Asp Gly Ser Lys Asp Thr Val Asp Val Thr Val Lys Val Val
                290                 295                 300

Asp Pro Arg Thr Asp Ala Asp Lys Asn Asp Pro Ala Gly Lys Asp Gln
305                 310                 315                 320

Gln Val Asn Val Gly Glu Thr Pro Lys Ala Glu Asp Ser Ile Gly Asn
                325                 330                 335

Leu Pro Asp Leu Pro Lys Gly Thr Thr Val Ala Phe Glu Thr Pro Val
                340                 345                 350

Asp Thr Ala Thr Pro Gly Asp Lys Pro Ala Lys Val Val Val Thr Tyr
                355                 360                 365

Pro Asp Gly Ser Lys Asp Thr Val Asp Val Thr Val Lys Val Val Asp
                370                 375                 380

Pro Arg Thr Asp Ala Asp Lys Asn Asp Pro Ala Gly Lys Asp Gln Gln
385                 390                 395                 400

Val Asn Val Gly Glu Thr Pro Lys Ala Glu Asp Ser Ile Gly Asn Leu
                405                 410                 415

Pro Asp Leu Pro Lys Gly Thr Thr Val Ala Phe Glu Thr Pro Val Asp
                420                 425                 430

Thr Ala Thr Pro Gly Asp Lys Pro Ala Lys Val Val Val Thr Tyr Pro
                435                 440                 445

Asp Gly Ser Lys Asp Thr Val Asp Val Thr Val Lys Val Val Asp Pro
450                 455                 460

Arg Thr Asp Ala Asp Lys Asn Asp Pro Ala Gly Lys Asp Gln Gln Val
465                 470                 475                 480

Asn Val Gly Glu Thr Pro Lys Ala Glu Asp Ser Ile Gly Asn Leu Pro
                485                 490                 495

Asp Leu Pro Lys Gly Thr Thr Val Ala Phe Glu Thr Pro Val Asp Thr
                500                 505                 510

Ala Thr Pro Gly Asp Lys Pro Ala Lys Val Val Val Thr Tyr Pro Asp
                515                 520                 525

Gly Ser Lys Asp Thr Val Asp Val Thr Val Lys Val Val Asp Pro Arg
530                 535                 540

Thr Asp Ala Asp Lys Asn Asp Pro Ala Gly Lys Asp Gln Gln Val Asn
545                 550                 555                 560

Val Gly Glu Thr Pro Lys Ala Glu Asp Ser Ile Gly Asn Leu Pro Asp
                565                 570                 575

Leu Pro Lys Gly Thr Thr Val Ala Phe Glu Thr Pro Val Asp Thr Ala
                580                 585                 590

Thr Pro Gly Asp Lys Pro Ala Lys Val Val Val Thr Tyr Pro Asp Gly
                595                 600                 605

Ser Lys Asp Thr Val Asp Val Thr Val Lys Val Val Asp Pro Arg Thr
                610                 615                 620

Asp Ala Asp Lys Asn Asp Pro Ala Gly Lys Asp Gln Gln Val Asn Val
625                 630                 635                 640
```

```
Gly Glu Thr Pro Lys Ala Glu Asp Ser Ile Gly Asn Leu Pro Asp Leu
            645                 650                 655

Pro Lys Gly Thr Thr Val Ala Phe Glu Thr Pro Val Asp Thr Ala Thr
            660                 665                 670

Pro Gly Asp Lys Pro Ala Lys Val Val Thr Tyr Pro Asp Gly Ser
            675                 680             685

Lys Asp Thr Val Asp Val Thr Val Lys Val Val Asp Pro Arg Thr Asp
            690                 695                 700

Ala Asp Lys Asn Asp Pro Ala Gly Lys Asp Gln Gln Val Asn Val Gly
705                 710                 715                 720

Glu Thr Pro Lys Ala Glu Asp Ser Ile Gly Asn Leu Pro Asp Leu Pro
                725                 730                 735

Lys Gly Thr Thr Val Ala Phe Glu Thr Pro Val Asp Thr Ala Thr Pro
                740                 745                 750

Gly Asp Lys Pro Ala Lys Val Val Thr Tyr Pro Asp Gly Ser Lys
                755                 760             765

Asp Thr Val Asp Val Thr Val Lys Val Val Asp Pro Arg Thr Asp Ala
                770                 775             780

Asp Lys Asn Asp Pro Ala Gly Lys Asp Gln Gln Val Asn Val Gly Glu
785             790                 795                 800

Thr Pro Lys Ala Glu Asp Ser Ile Gly Asn Leu Pro Asp Leu Pro Lys
                805                 810                 815

Gly Thr Thr Val Ala Phe Glu Thr Pro Val Asp Thr Ala Thr Pro Gly
                820                 825                 830

Asp Lys Pro Ala Lys Val Val Thr Tyr Pro Asp Gly Ser Lys Asp
                835                 840             845

Thr Val Asp Val Thr Val Lys Val Val Asp Pro Arg Thr Asp Ala Asp
850                 855                 860

Lys Asn Asp Pro Ala Gly Lys Asp Gln Gln Val Asn Val Gly Glu Thr
865             870                 875                 880

Pro Lys Ala Glu Asp Ser Ile Gly Asn Leu Pro Asp Leu Pro Lys Gly
                885                 890                 895

Thr Thr Val Ala Phe Glu Thr Pro Val Asp Thr Ala Thr Pro Gly Asp
                900                 905                 910

Lys Pro Ala Lys Val Val Thr Tyr Pro Asp Gly Ser Lys Asp Thr
                915                 920             925

Val Asp Val Thr Val Lys Val Val Asp Pro Arg Thr Asp Ala Asp Lys
                930                 935                 940

Asn Asp Pro Ala Gly Lys Asp Gln Gln Val Asn Val Gly Glu Thr Pro
945                 950                 955                 960

Lys Ala Glu Asp Ser Ile Gly Asn Leu Pro Asp Leu Pro Lys Gly Thr
                965                 970                 975

Thr Val Ala Phe Glu Thr Pro Val Asp Thr Ala Thr Pro Gly Asp Lys
                980                 985                 990

Pro Ala Lys Val Val Thr Tyr  Pro Asp Gly Ser Lys  Asp Thr Val
            995                 1000                1005

Asp Val  Thr Val Lys Val Val  Asp Pro Arg Thr Asp  Ala Asp Lys
        1010                1015                1020

Asn Asp  Pro Ala Gly Lys Asp  Gln Gln Val Asn Val  Gly Glu Thr
        1025                1030                1035

Pro Lys  Ala Glu Asp Ser Ile  Gly Asn Leu Pro Asp  Leu Pro Lys
        1040                1045                1050
```

```
Gly Thr Thr Val Ala Phe Glu Thr Pro Val Asp Thr Ala Thr Pro
    1055                1060                1065

Gly Asp Lys Pro Ala Lys Val Val Thr Tyr Pro Asp Gly Ser
1070                1075                1080

Lys Asp Thr Val Asp Val Thr Val Lys Val Val Asp Pro Arg Thr
    1085                1090                1095

Asp Ala Asp Lys Asn Asp Pro Ala Gly Lys Asp Gln Gln Val Asn
    1100                1105                1110

Val Gly Glu Thr Pro Lys Ala Glu Asp Ser Ile Gly Asn Leu Pro
    1115                1120                1125

Asp Leu Pro Lys Gly Thr Thr Val Ala Phe Glu Thr Pro Val Asp
    1130                1135                1140

Thr Ala Thr Pro Gly Asp Lys Pro Ala Lys Val Val Val Thr Tyr
    1145                1150                1155

Pro Asp Gly Ser Lys Asp Thr Val Asp Val Thr Val Lys Val Val
    1160                1165                1170

Asp Pro Arg Thr Asp Ala Asp Lys Asn Asp Pro Ala Gly Lys Asp
    1175                1180                1185

Gln Gln Val Asn Gly Lys Gly Asn Lys Leu Pro Ala Thr Gly Glu
    1190                1195                1200

Asn Ala Thr Pro Phe Phe Asn Val Val Ala Leu Thr Ile Met Ser
    1205                1210                1215

Ser Val Gly Leu Leu Ser Val Ser Lys Lys Lys Glu Asp
    1220                1225                1230

<210> SEQ ID NO 5
<211> LENGTH: 237
<212> TYPE: DNA
<213> ORGANISM: Group B Streptococcus - Strain BM110
<220> FEATURE:
<221> NAME/KEY: CDS
<222> LOCATION: (1)..(237)
<223> OTHER INFORMATION:

<400> SEQUENCE: 5 gat gcc gat aag aat gat cca gca ggt aaa gat cag caa gtc aat gta    48
Asp Ala Asp Lys Asn Asp Pro Ala Gly Lys Asp Gln Gln Val Asn Val
1               5                   10                  15 ggt gag aca ccg aag gca gaa gat tct att ggt aac tta cca gat ctt    96
Gly Glu Thr Pro Lys Ala Glu Asp Ser Ile Gly Asn Leu Pro Asp Leu
            20                  25                  30 ccg aaa ggt aca aca gta gcc ttt gaa act cca gtt gat acg gca aca   144
Pro Lys Gly Thr Thr Val Ala Phe Glu Thr Pro Val Asp Thr Ala Thr
        35                  40                  45 ccg gga gac aaa cca gca aaa gtt gtt gtg act tac cca gat ggt tca   192
Pro Gly Asp Lys Pro Ala Lys Val Val Val Thr Tyr Pro Asp Gly Ser
    50                  55                  60 aaa gat act gta gat gtg act gtt aag gtt gtc gat cca cgt aca        237
Lys Asp Thr Val Asp Val Thr Val Lys Val Val Asp Pro Arg Thr
65                  70                  75

<210> SEQ ID NO 6
<211> LENGTH: 79
<212> TYPE: PRT
<213> ORGANISM: Group B Streptococcus - Strain BM110

<400> SEQUENCE: 6

Asp Ala Asp Lys Asn Asp Pro Ala Gly Lys Asp Gln Gln Val Asn Val
1               5                   10                  15
```

```
Gly Glu Thr Pro Lys Ala Glu Asp Ser Ile Gly Asn Leu Pro Asp Leu
            20                  25                  30

Pro Lys Gly Thr Thr Val Ala Phe Glu Thr Pro Val Asp Thr Ala Thr
        35                  40                  45

Pro Gly Asp Lys Pro Ala Lys Val Val Thr Tyr Pro Asp Gly Ser
    50                  55                  60

Lys Asp Thr Val Asp Val Thr Val Lys Val Val Asp Pro Arg Thr
65                  70                  75

<210> SEQ ID NO 7
<211> LENGTH: 25
<212> TYPE: DNA
<213> ORGANISM: Artificial Sequence
<220> FEATURE:
<223> OTHER INFORMATION: Primer targeted to Group B Streptococcus

<400> SEQUENCE: 7
tgactaaaaa tgttcagaat ggtag                                   25

<210> SEQ ID NO 8
<211> LENGTH: 25
<212> TYPE: DNA
<213> ORGANISM: Artificial Sequence
<220> FEATURE:
<223> OTHER INFORMATION: Primer targeted to Group B Streptococcus

<400> SEQUENCE: 8
gaaacagata ataaaccaac tgatg                                   25

<210> SEQ ID NO 9
<211> LENGTH: 1020
<212> TYPE: PRT
<213> ORGANISM: Group B Streptococcus - Strain A909

<400> SEQUENCE: 9

Met Phe Arg Arg Ser Lys Asn Asn Ser Tyr Asp Thr Ser Gln Thr Lys
1               5                   10                  15

Gln Arg Phe Ser Ile Lys Lys Phe Lys Phe Gly Ala Ala Ser Val Leu
            20                  25                  30

Ile Gly Leu Ser Phe Leu Gly Gly Val Thr Gln Gly Asn Leu Asn Ile
        35                  40                  45

Phe Glu Glu Ser Ile Val Ala Ala Ser Thr Ile Pro Gly Ser Ala Ala
    50                  55                  60

Thr Leu Asn Thr Ser Ile Thr Lys Asn Ile Gln Asn Gly Asn Ala Tyr
65                  70                  75                  80

Ile Asp Leu Tyr Asp Val Lys Leu Gly Lys Ile Asp Pro Leu Gln Leu
                85                  90                  95

Ile Val Leu Glu Gln Gly Phe Thr Ala Lys Tyr Val Phe Arg Gln Gly
            100                 105                 110

Thr Lys Tyr Tyr Gly Asp Val Ser Gln Leu Thr Ser Thr Gly Arg Ala
        115                 120                 125

Ser Leu Thr Tyr Asn Ile Phe Gly Glu Asp Gly Leu Pro His Val Lys
    130                 135                 140

Thr Asp Gly Gln Ile Asp Ile Val Ser Val Ala Leu Thr Ile Tyr Asp
145                 150                 155                 160

Ser Thr Thr Leu Arg Asp Lys Ile Glu Glu Val Arg Thr Asn Ala Asn
                165                 170                 175

Asp Pro Lys Trp Thr Glu Glu Ser Arg Thr Glu Val Leu Thr Gly Leu
            180                 185                 190
```

-continued

```
Asp Thr Ile Lys Thr Asp Ile Asp Asn Asn Pro Lys Thr Gln Thr Asp
            195                 200                 205

Ile Asp Ser Lys Ile Val Glu Val Asn Glu Leu Glu Lys Leu Leu Val
        210                 215                 220

Leu Ser Val Pro Asp Lys Asp Lys Tyr Asp Pro Thr Gly Gly Glu Thr
225                 230                 235                 240

Thr Val Pro Gln Gly Thr Pro Val Ser Asp Lys Glu Ile Thr Asp Leu
                245                 250                 255

Val Lys Ile Pro Asp Gly Ser Lys Gly Val Pro Thr Val Gly Asp
            260                 265                 270

Arg Pro Asp Thr Asn Val Pro Gly Asp His Val Ala Thr Val Glu Val
            275                 280                 285

Thr Tyr Pro Asp Gly Thr Lys Asp Thr Val Glu Val Thr Val His Val
        290                 295                 300

Thr Pro Lys Pro Val Pro Asp Lys Asp Lys Tyr Asp Pro Thr Gly Gly
305                 310                 315                 320

Glu Thr Thr Val Pro Gln Gly Thr Pro Val Ser Asp Lys Glu Ile Thr
                325                 330                 335

Asp Leu Val Lys Ile Pro Asp Gly Ser Lys Gly Val Pro Thr Val Val
            340                 345                 350

Gly Asp Arg Pro Asp Thr Asn Val Pro Gly Asp His Val Ala Thr Val
            355                 360                 365

Glu Val Thr Tyr Pro Asp Gly Thr Lys Asp Thr Val Glu Val Thr Val
        370                 375                 380

His Val Thr Pro Lys Pro Val Pro Asp Lys Asp Lys Tyr Asp Pro Thr
385                 390                 395                 400

Gly Gly Glu Thr Thr Val Pro Gln Gly Thr Pro Val Ser Asp Lys Glu
                405                 410                 415

Ile Thr Asp Leu Val Lys Ile Pro Asp Gly Ser Lys Gly Val Pro Thr
            420                 425                 430

Val Val Gly Asp Arg Pro Asp Thr Asn Val Pro Gly Asp His Val Ala
            435                 440                 445

Thr Val Glu Val Thr Tyr Pro Asp Gly Thr Lys Asp Thr Val Glu Val
        450                 455                 460

Thr Val His Val Thr Pro Lys Pro Val Pro Asp Lys Asp Lys Tyr Asp
465                 470                 475                 480

Pro Thr Gly Gly Glu Thr Thr Val Pro Gln Gly Thr Pro Val Ser Asp
                485                 490                 495

Lys Glu Ile Thr Asp Leu Val Lys Ile Pro Asp Gly Ser Lys Gly Val
            500                 505                 510

Pro Thr Val Val Gly Asp Arg Pro Asp Thr Asn Val Pro Gly Asp His
            515                 520                 525

Val Ala Thr Val Glu Val Thr Tyr Pro Asp Gly Thr Lys Asp Thr Val
530                 535                 540

Glu Val Thr Val His Val Thr Pro Lys Pro Val Pro Asp Lys Asp Lys
545                 550                 555                 560

Tyr Asp Pro Thr Gly Gly Glu Thr Thr Val Pro Gln Gly Thr Pro Val
                565                 570                 575

Ser Asp Lys Glu Ile Thr Asp Leu Val Lys Ile Pro Asp Gly Ser Lys
            580                 585                 590

Gly Val Pro Thr Val Val Gly Asp Arg Pro Asp Thr Asn Val Pro Gly
            595                 600                 605
```

-continued

```
Asp His Val Ala Thr Val Glu Val Thr Tyr Pro Asp Gly Thr Lys Asp
    610             615                 620

Thr Val Glu Val Thr Val His Val Thr Pro Lys Pro Val Pro Asp Lys
625                 630                 635                 640

Asp Lys Tyr Asp Pro Thr Gly Gly Glu Thr Thr Val Pro Gln Gly Thr
                645                 650                 655

Pro Val Ser Asp Lys Glu Ile Thr Asp Leu Val Lys Ile Pro Asp Gly
            660                 665                 670

Ser Lys Gly Val Pro Thr Val Val Gly Asp Arg Pro Asp Thr Asn Val
        675                 680                 685

Pro Gly Asp His Val Ala Thr Val Glu Val Thr Tyr Pro Asp Gly Thr
    690                 695                 700

Lys Asp Thr Val Glu Val Thr Val His Val Thr Pro Lys Pro Val Pro
705                 710                 715                 720

Asp Lys Asp Lys Tyr Asp Pro Thr Gly Gly Glu Thr Thr Val Pro Gln
                725                 730                 735

Gly Thr Pro Val Ser Asp Lys Glu Ile Thr Asp Leu Val Lys Ile Pro
            740                 745                 750

Asp Gly Ser Lys Gly Val Pro Thr Val Val Gly Asp Arg Pro Asp Thr
        755                 760                 765

Asn Val Pro Gly Asp His Val Ala Thr Val Glu Val Thr Tyr Pro Asp
    770                 775                 780

Gly Thr Lys Asp Thr Val Glu Val Thr Val His Val Thr Pro Lys Pro
785                 790                 795                 800

Val Pro Asp Lys Asp Lys Tyr Asp Pro Thr Gly Gly Glu Thr Thr Val
                805                 810                 815

Pro Gln Gly Thr Pro Val Ser Asp Lys Glu Ile Thr Asp Leu Val Lys
            820                 825                 830

Ile Pro Asp Gly Ser Lys Gly Val Pro Thr Val Val Gly Asp Arg Pro
        835                 840                 845

Asp Thr Asn Val Pro Gly Asp His Val Ala Thr Val Glu Val Thr Tyr
    850                 855                 860

Pro Asp Gly Thr Lys Asp Thr Val Glu Val Thr Val His Val Thr Pro
865                 870                 875                 880

Lys Pro Val Pro Asp Lys Asp Lys Tyr Asp Pro Thr Gly Gly Glu Thr
                885                 890                 895

Thr Val Pro Gln Gly Thr Pro Val Ser Asp Lys Glu Ile Thr Asp Leu
            900                 905                 910

Val Lys Ile Pro Asp Gly Ser Lys Gly Val Pro Thr Val Val Gly Asp
        915                 920                 925

Arg Pro Asp Thr Asn Val Pro Gly Asp His Val Ala Thr Val Glu Val
    930                 935                 940

Thr Tyr Pro Asp Gly Thr Lys Asp Thr Val Glu Val Thr Val His Val
945                 950                 955                 960

Thr Pro Lys Pro Val Pro Asp Lys Asp Lys Tyr Asp Pro Thr Gly Lys
                965                 970                 975

Ala Gln Gln Val Asn Gly Lys Gly Asn Lys Leu Pro Ala Thr Gly Glu
            980                 985                 990

Asn Ala Thr Pro Phe Phe Asn Val  Ala Ala Leu Thr Ile  Ile Ser Ser
            995                 1000                1005

Val Gly  Leu Leu Ser Val Ser  Lys Lys Lys Glu Asp
    1010                1015                1020
```

PROTEIN RIB, A CELL SURFACE PROTEIN THAT CONFERS IMMUNITY TO MANY STRAINS OF THE GROUP B STREPTOCOCCUS: PROCESS FOR PURIFICATION OF THE PROTEIN, REAGENT KIT AND PHARMACEUTICAL COMPOSITION

This application is a divisional of application Ser. No. 08/904,263, filed on Jul. 31, 1997 now U.S. Pat. No. 6,015,889, U.S. application Ser. No. 08/904,263 is a continuation-in-part application of U.S. application Ser. No. 08/487,675 filed on Jun. 7, 1995 and issued as U.S. Pat. No. 5,869,064 on Feb. 9, 1999. U.S. application Ser. No. 08/487,675 is a continuation application of International Application PCT/SE94/00246 filed Mar. 24, 1994. The entire contents of these applications are hereby incorporated by reference.

This invention relates to a novel protein designated Rib (and subfragments, variants and multiples thereof) which confers immunity to most invasive strains of the group B Streptococcus, DNA sequences encoding the protein or functional fragments or domains of the protein, DNA sequences which hybridize under stringent conditions to the DNA encoding the protein, a procedure for purification of the protein, antibodies specific to the protein, a reagent kit and a pharmaceutical composition comprising the protein or fragments thereof.

During the last three decades, the group B Streptococcus has emerged as a major cause of neonatal disease in the Western world. In the United States alone, there are about 10,000 cases per year of invasive disease caused by this bacterium. These infections have an overall mortality of about 20%, and many of the infants that survive have permanent neurological sequelae. In view of these findings, a large effort has been made to find methods of prevention and treatment and to analyze the mechanisms by which group B streptococci cause infections.

About 20% of all women are vaginal carriers of the group B Streptococcus, and vertical transmission from the maternal genital tract is probably the most common source of infection in neonatal disease caused by this bacterium. However, only 1 to 2% of the infants that are colonized by the group B Streptococcus at birth are afflicted by serious infection. Other factors than exposure to the bacterium during birth must therefore contribute to the development of neonatal disease. Mothers of infected infants have significantly lower levels of antibodies to the type III capsule, which implies that these antibodies are important for protection against neonatal disease (Baker, C. J. and D. L. Kasper, N. Engl. J. Med. 1976, 294:753).

Group B streptococcal strains are divided into four major serotypes (Ia, Ib, II, and III) based on the structure of the polysaccharide capsule (Baker, J Inf Dis 1990. 161: 917). Serotypes I, II, and III occur in roughly equal proportions among strains in the normal flora, but type III accounts for about two-thirds of all isolates from invasive infections. Since the capsule is a known virulence factor, it has been studied in considerable detail, in particular in type III strains. Efforts have been made to develop a vaccine, in which the type III polysaccharide capsule would be an essential component. However, use of the polysaccharide capsule as a vaccine may give problems due to crossreactions with human tissues (Pritchard et al., Infect Immun 1992. 60: 1598). It would therefore be very valuable if one could develop a vaccine based on proteins rather than on polysaccharides.

The group B Streptococcus can also cause mastitis in cows, a bovine disease that is of considerable economical importance. Development of a vaccine against group B streptococcal infections is therefore of interest also in veterinary medicine.

Two group B streptococcal cell surface proteins have previously been studied in detail: the alpha and beta proteins. These proteins confer protective immunity to strains expressing the proteins, but they are of limited interest for group B streptococcal disease, since they are usually not expressed by type III strains, which cause the majority of serious infections.

The present invention relates to a streptococcal cell surface protein, and variants and subfragments thereof. This protein, which is designated protein Rib, was isolated from a group B streptococcal strain of serotype III as a distinct 95 kD protein. Protein Rib is expressed by almost all group B streptococcal strains of serotype III and by a few strains of other serotypes such as II. A method has been devised to purify protein Rib and it has been demonstrated that antibodies to this protein protect against lethal infection with strains expressing protein Rib.

The invention also relates to naturally occurring and artificially modified variants, subfragments and multiples of the Rib protein which have the ability to protect against infections caused by protein Rib expressing bacteria, i.e., especially group B streptococcal strains of serotype III.

The invention also relates to a vector, such as a plasmid, a cosmid or a phage, containing the genetic code for protein Rib and variants, subfragments and fragments thereof, suitable for insertion in a non-human host organism and expression from said host. The invention particularly relates to three phage clones, lambda Rib1-3, lambda Rib1-5 and lambda Rib1-7, having deposit numbers DSM 9039, DSM 9040 and DSM 9041, respectively.

The invention also relates to a DNA sequence encoding protein Rib and variants, subfragments fragments and multiples thereof, that may be inserted in a suitable vector, such as a plasmid, a cosmid or a phage. The DNA sequence can be obtained from the deposited phages lambda Rib1-3, lambda Rib1-5 och lambda Rib1-7.

The Rib protein is expressed by different type III strains. Extracts prepared from several different strains that were analyzed by Western blotting, using anti-Rib serum for the analysis, showed that almost all extracts contained protein Rib, but the molecular mass of the protein varied between 65 and 125 kD (data not shown). This result was not unexpected, since size variation has previously been described also for other group B streptococcal proteins, the alpha and beta proteins.

The available data suggest that the protein may consist of multiples of units, each unit corresponding to a molecular mass of about 9 kD. The invention therefore includes subfragments and multiples of the 95 kD protein or of a basic unit with the same characteristics. Variants include substitution or insertions of amino acids without changing the ability to protect against infections caused by bacterias expressing the protein.

Group B streptococcal strains are well known and may be isolated from the blood of infected human beings. The BM110 strain used by the inventors was obtained from Dr. S. Mattingly (University of Texas, San Antonio, Tex.). All strains referred to herein are obtainable from the inventors at the University of Lund and the Lund University Hospital (Doctor Gunnar Lindahl, Department of Medical Microbiology, Sölvegatan 23, S 22362 Lund, Sweden).

Protein Rib may be isolated from group B streptococcal strains of serotype III, preferably from strain BS30 or BM110. The invention concerns a process for purification of protein Rib.

The protein may be isolated by the following procedure: A Streptococcus Group B strain expressing the protein is cultivated, the medium and/or the microorganism are isolated, the bacteria are digested with an enzyme, preferably mutanolysin, a protease inhibitor is optionally added, the digested bacteria are separated from the supernatant and protein Rib is extracted from the supernatant. The media can be any media suitable for cultivation of streptococci; such as Todd-Hewitt broth (Oxoid) and the cells are preferably cultivated 1–30, especially 12–20 hours. The digestion with an enzyme, preferably mutanolysin, is performed without shaking for 1–30, especially 10–20, preferably 15–18 hours at 20–40° C., preferably 37° C. The protein may be isolated from the medium, and in such a case there is no need for digestion with the enzyme which is used to break the cell walls. A protease inhibitor such as benzamidine chloride, iodoacetic acid or phenylmethyl sulfonyl fluoride is added to prevent the action from proteases which may contaminate the mutanolysin or may be present in the microorganisms.

The protein can be purified by ion exchange chromatography, preferably anion exchange chromatography and gel filtration, and fractions containing the protein collected according to established practice within the art.

The invention especially concerns a substantially pure protein Rib or subfragments thereof. With the expression "substantially pure" we understand a substance that does not contain pharmaceutically harmful substances.

The invention also concerns antibodies corresponding to protein Rib and subfragments, variants or multiples thereof. It is well known how to immunize an animal with an antigen, in this case protein Rib, collect the blood, isolate the serum and use the antibodies that react with the protein. The serum or an IgG fraction containing the antibodies may be used in analyzing the protein.

Since antibodies to protein Rib can protect against lethal infection with group B streptococcal strains, a method to measure the level of such antibodies can be valuable, for example in order to estimate if a pregnant woman has antibodies enough to protect the baby from such an infection. Protein Rib or subfragments thereof can be used to detect such antibodies to the protein. The invention therefore also concerns a reagent kit containing protein Rib or subfragments thereof.

The present invention further includes a method of immunizing an animal such as a rodent or human with the purified Rib protein. Pharmaceutical compositions containing either Rib protein or fragments or variants thereof which confer immunity against Group B streptococcal type III proteins or antibodies which recognize Rib protein are further contemplated by the present invention. Such pharmaceutical compositions further comprise suitable pharmaceutical carriers.

It can also be of interest to analyze various samples for the presence of protein Rib. Antibodies to the protein can be used for this purpose. The invention therefore also concerns a reagent kit, comprising antibodies to protein Rib or subfragments thereof, for detection of the protein. A reagent kit may contain any of the above mentioned blood fractions containing the antibodies. It may also contain the protein, subfragments or multiples thereof for use as a standard.

The properties of protein Rib indicate that this protein can be used for the development of a vaccine against the group B Streptococcus. The invention therefore also concerns a pharmaceutical composition comprising the protein or fragments thereof as active ingredients, possibly together with pharmaceutically acceptable adjuvants and excipients. Suitable pharmaceutically acceptable adjuvants are those conventionally used in this field. Examples of suitable excipients are mannitol, lactose, starch, cellulose, glucose, etc., only to mention a few. The examples given of the adjuvant and the excipients are not to be regarded as limiting the invention.

The invention will now be described in more detail, with the accompanying drawings, in which:

BRIEF DESCRIPTION OF THE DRAWINGS

FIGS. 7A and B Nucleotide sequence (SEQ ID NO: 3) of the rib gene from strain BM110 and deduced amino acid sequence (SEQ ID NO: 4). The sequence is divided into a 5' part, a central part with 12 identical repeats and a partial repeat, and a 3' part. The box indicates a possible ribosomal binding site. The vertical arrow indicates the end of the signal sequence. The dashed line indicates the NH$_2$-terminal sequence determined for protein Rib from strain BM110. The horizontal arrows indicate the position of the repeats as well as of a partial repeat. The sequence data have been submitted to the GenBank™ data base (accession no U58333).

FIGS. 9A and 9B. Comparison of the Rib and α proteins. FIG. 9A shows the alignment of the amino acid sequences of Rib (SEQ ID NO: 4) from strain BM110 and α (SEQ ID NO: 9) from strain A909. The two vertical arrows indicate the ends of the signal sequences. The repeat regions are shown in the shaded box. Only one full repeat from each protein is shown, followed by the partial repeat. FIG. 9B shows the overall structure of Rib from strain BM110 and α from strain A909 and degree of amino acid residue identity between different regions of the proteins. S, signal peptide; N, NH$_2$-terminal region; R, one repeat; P, partial repeat; C, COOH-terminal region. The number of amino acids in each region is indicated. The Rib protein has 12 repeats of 79 amino acids and the α protein has 9 repeats of 82 amino acids.

FIG. 10A, binding of anti-Rib serum to immobilized Rib. FIG. 10B, binding of anti-α serum to immobilized α.

FIG. 11A, relationship between acrylamide concentration and apparent molecular mass in SDS-PAGE. FIGS. 11B and 11C, stained SDS-PAGE gels of purified Rib, α and β proteins analyzed at acrylamide concentrations of 5% (FIG. 11B) and 10% (FIG. 11C). The preparations of Rib and α give rise to one major band and one minor band. The molecular mass was determined for the major band. Molecular mass markers (in KDa) are shown to the right in each gel.

FIG. 12A, Western blot analysis of purified preparations of the Rib, α and β proteins under standard conditions, using specific rabbit antisera. Molecular mass markers are in kDa. FIG. 12B, proteins adjusted to pH 4.0 and then boiled with sample buffer for 5 min. Stained gel, 10% acrylamide. FIG. 12C, proteins adjusted to pH 4.0 and then boiled with sample buffer for 15 min. Stained tricine gel, 16.5% acrylamide. In gels of FIGS. 12B and 12C, molecular mass markers (in kDa) are included in the figure. FIG. 12D, overall structure of the mature Rib and α proteins. Amino-terminal sequences and putative acid-sensitive Asp-Pro (DP) sites are indicated. The bars denoted a–d show possible structures for the fragments indicated in FIGS. 12B and 12C. N, NH$_2$-terminal non-repeated region; R, one repeat.

Figure 1A:
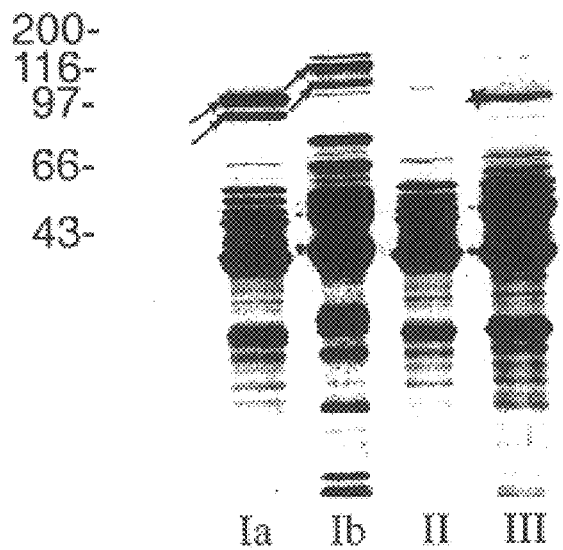
FIGS. 1A and B show a Western blot analysis of extracts prepared from group B streptococcal strains representing the four main serotypes (type Ia: strain A909; type Ib: SB3S; type II: B1284; type III: BS30). As shown in the immunoblot, the strains of types Ia and Ib express the alpha and beta proteins, and the positions of these proteins in the stained gel are indicated by arrows (lower arrow: alpha antigen; upper arrow: beta antigen). The position in the stained gel of the 95-kD protein Rib of the type III strain BS30 is indicated by a star. Molecular mass markers, indicated on the left, are in kD.
Figure 1B:
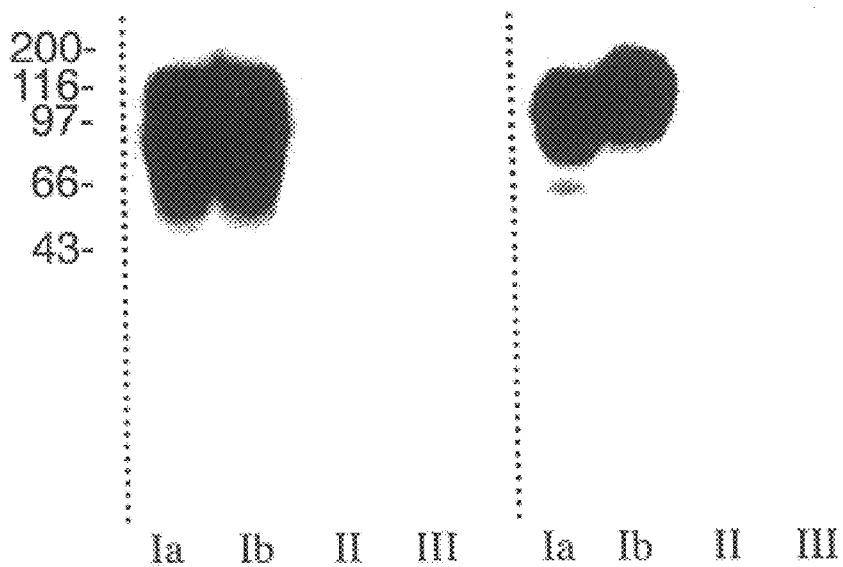
Figure 2A:
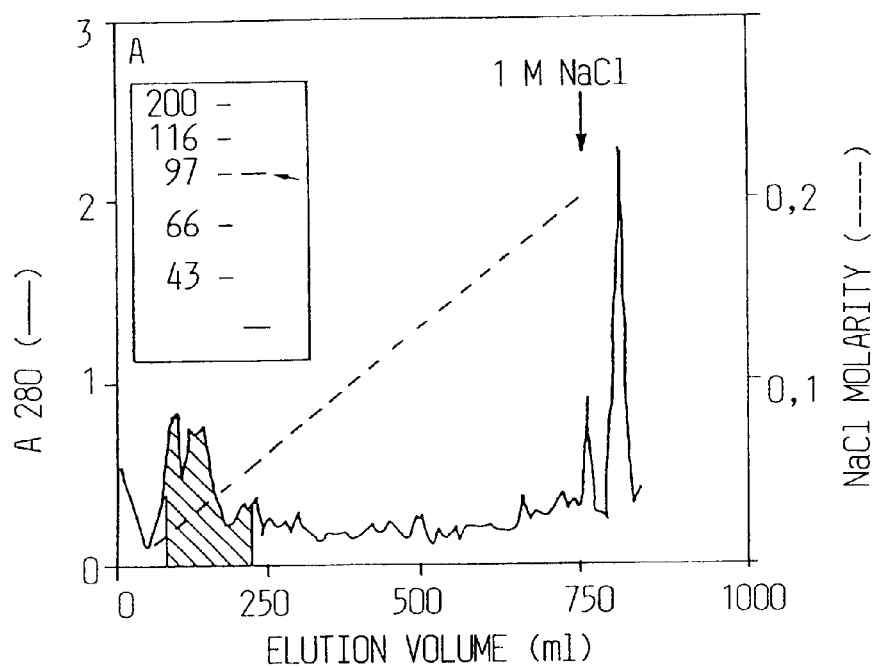
FIGS. 2A and 2B show purification of protein Rib from the type III strain BS30. (A) A mutanolysin extract, partially purified through a previous step of DEAE ion exchange chromatography, was subjected to ion exchange chromatography on a 30 ml column of DEAE Bio-Gel A, which was eluted with a linear gradient (800 ml) of NaCl in 10 mM Tris, pH 8.0, followed by 1 M NaCl (60 ml). The shaded area indicates fractions containing protein Rib. The insert shows a pool of the protein Rib-containing fractions analyzed by SDS-PAGE; molecular mass markers, indicated on the left, are in kD, and the position of protein Rib (95 kD) is indicated by an arrow. (B) The pool of protein Rib-containing fractions from the ion exchange chromatography was subjected to gel filtration on a column (4.2×90 cm) of Sepharose CL6B. The shaded area indicates fractions containing protein Rib and the insert shows a pool of these fractions analyzed by SDS-PAGE. $V_o$, void volume; $V_t$, total volume.
Figure 2B:
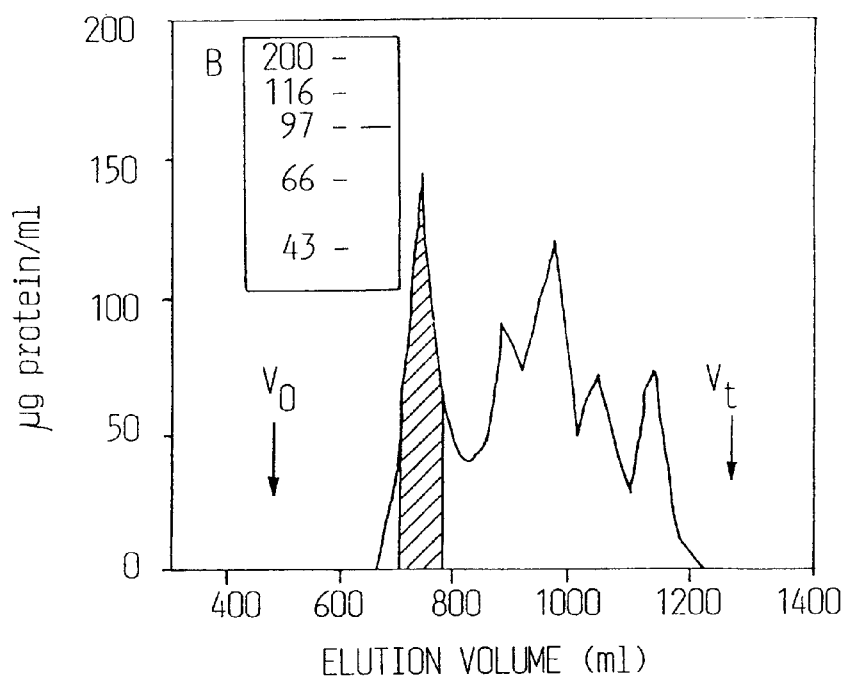

Mutanolysin extracts of several strains of different serotypes were analyzed by SDS-PAGE and by immunoblotting, using antisera to the alpha and beta proteins, see example 1. Results obtained with four strains representing the four major serotypes are shown in FIG. 1. The alpha and beta proteins, which are expressed by both the type Ia strain and the type Ib strain, gave rise to distinct bands in the high molecular weight region of the stained gel. These proteins vary in size between the two strains, in agreement with previous observations. A major protein species in the high molecular weight region was present also in the extract prepared from the type III strain, although this strain does not express the alpha protein or the beta protein. Such a distinct protein species of high molecular weight was also observed in extracts of other type III strains, and the protein appeared to vary in size between different strains. These similarities to the alpha and beta proteins made it of interest to study the high molecular weight proteins of type III strains in more detail. Strain BS30 was chosen for this work, because it was known to be mouse virulent. The 95-kD protein expressed by this strain (FIG. 1) was purified (Example 2) from mutanolysin extracts, using two consecutive steps of ion exchange chromatography, followed by gel filtration (FIG. 2). Fractions were analyzed by SDS-PAGE for presence of the 95-kD protein. When appropriate fractions from the gel filtration were pooled and analyzed, only two protein species were found: a major 95-kD protein and a minor 90-kD protein (see insert in FIG. 2B). The 90-kD protein most likely represents a degradation product of the 95-kD protein, since these two proteins were later shown to have the same NH$_2$-terminal sequence. The purified protein is referred to as protein Rib (resistance to proteases, immunity, group B). Antiserum to the 95-kD form of protein Rib was prepared by immunizing rabbits with slices cut out from SDS-PAGE gels.

To analyze whether protein Rib is a cell surface protein, strains representing the four major serotypes were tested for ability to bind anti-Rib serum (FIG. 3). The five strains studied included the four strains described above and an additional type III strain, BM110, which is a member of the high-virulence type III clone. For comparison, these five strains were also tested for expression of the alpha and beta proteins, using antisera to highly purified preparations of these proteins.

Figure 3A:
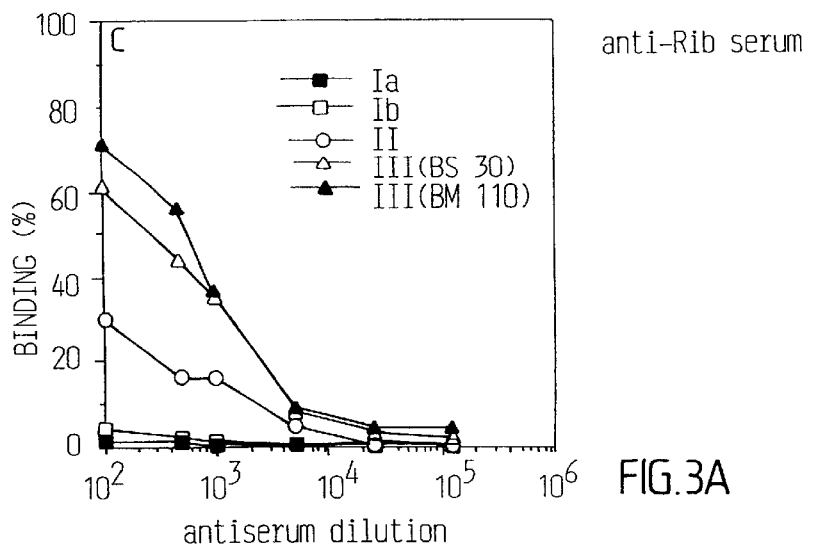
FIGS. 3A, 3B and 3C show analysis of group B streptococcal strains of the four major serotypes for cell surface expression of the alpha, beta and Rib proteins. Five strains were tested: A909 (type Ia); SB35 (type Ib); B1284 (type II); BS30 (type III), and BM110 (type III). The symbols used for these five strains are shown in panel C. Bacterial suspensions were incubated with different dilutions of rabbit antiserum to the alpha, beta, or Rib protein, as indicated. The numbers on the x-axis refer to final antibody dilution in the bacterial mixture. Bound antibodies were detected by incubation with radiolabelled protein G. Controls with preimmune rabbit serum were included in all experiments and were completely negative in all cases.
Figure 3B:
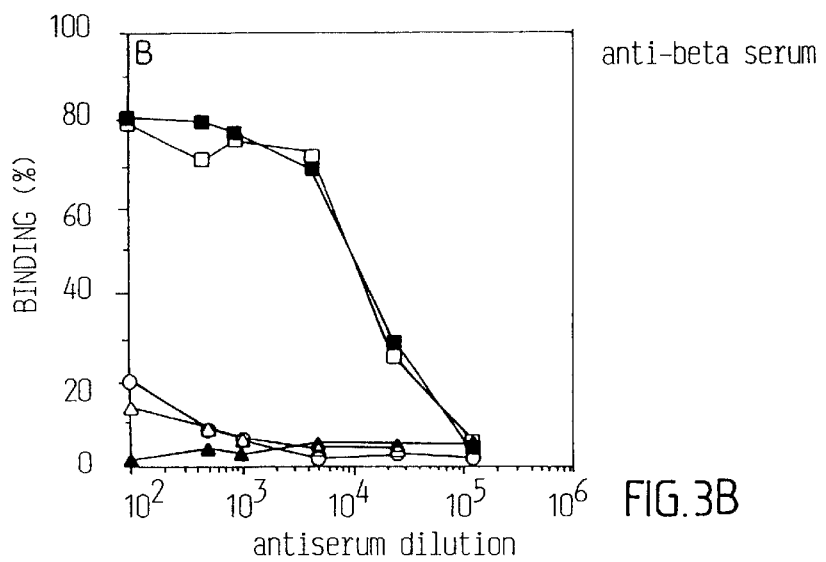

The anti-alpha serum reacted strongly with the Ia and Ib strains, as expected, and it also reacted weakly with the two strains of type III (FIG. 3A). However, mutanolysin extracts of the type III strains did not contain any detectable alpha protein, when analyzed in a Western blot. It therefore seems likely that this weak reactivity of anti-alpha serum with whole bacteria of type III represents a cross-reactivity with some other cell wall component. These data show that reactivity with anti-alpha serum can be used to unequivocally analyze whether a strain expresses the alpha antigen on the cell surface. Similar data were obtained with anti-beta serum (FIG. 3B).

Figure 3C:
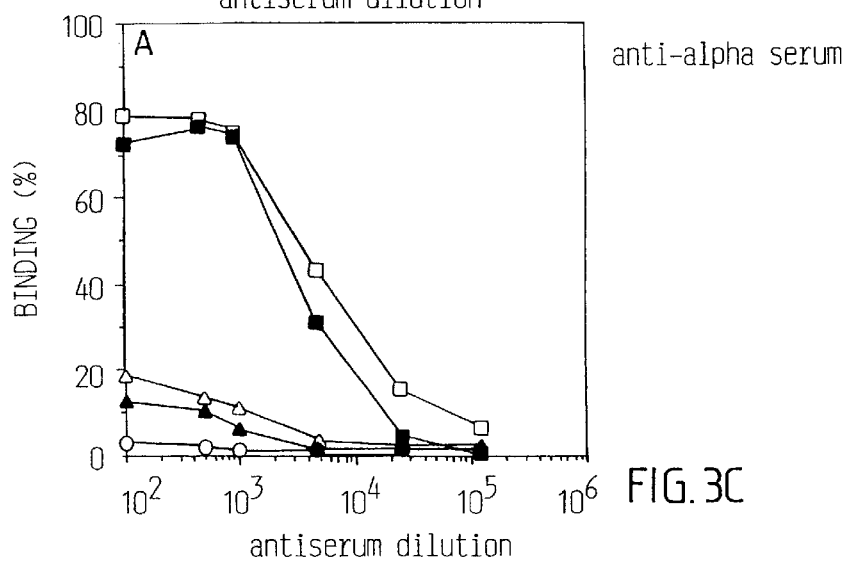

The antiserum to protein Rib reacted with the two type III strains, but not with the type Ia and Ib strains (FIG. 3C). An intermediate level of binding was observed for the type II strain. When mutanolysin extracts of the five strains were analyzed in a Western blot experiment, using anti-Rib serum for the analysis, the extracts of the type III strains reacted strongly, giving major blotting bands at 95 kD, but the extracts of the three other strains completely lacked reactivity (data not shown). This result indicates that the intermediate reactivity of anti-Rib serum with the type II strain was due to a crossreactivity, which disappeared under the conditions of the Western blot. We conclude that protein Rib is expressed on the cell surface of the two type III strains, but not on the other three strains.

A total of 58 strains of known serotype, all of which had been isolated from invasive infections, were then tested for ability to bind antibodies to protein Rib (see Table 1, example 6). Each strain was also tested for binding of antibodies to the alpha and beta proteins. To simplify the study of many strains, each antiserum was tested at a single 1000-fold dilution, chosen on the basis of the data shown in FIG. 3. This type of analysis gave unequivocal results, summarized in Table 1 of example 6. Protein Rib was found on the cell surface of 31 out of 33 type III strains and on one out of 13 type II strains, but not on any of the 12 strains of types Ia and Ib.

It seemed possible that strains lacking protein Rib on the cell surface excrete the protein into the medium. Culture supernatants of the 58 strains listed in Table 1 were therefore analyzed in a dot-blot experiment, using anti-Rib serum for the analysis. Protein Rib was not detected in the supernatants of any of the 26 strains that do not express the protein on the cell surface, but was found in the supernatants of 26 of the 32 strains expressing the protein on the cell surface (data not shown).

A mouse protection model was used to study whether rabbit antibodies to protein Rib can protect against lethal infection with the group B Streptococcus (Table 2, Example 7). Control animals received antiserum to the alpha protein or preimmune serum, as indicated. The data show that antiserum to protein Rib protects mice against lethal infection with strains expressing protein Rib.

Figure 4A:
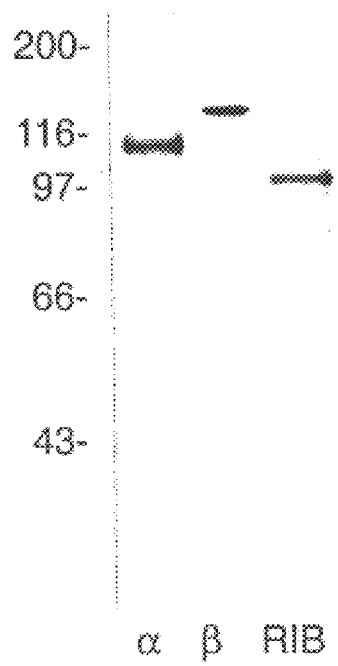
FIGS. 4A and B show Western blot analysis of purified alpha, beta, and Rib proteins with rabbit antisera raised against the purified proteins. Antisera were used at a 1:1,000 dilution, and bound antibodies were detected with radiolabelled protein G. Molecular mass markers, indicated on the left, are in kD.
Figure 4B:
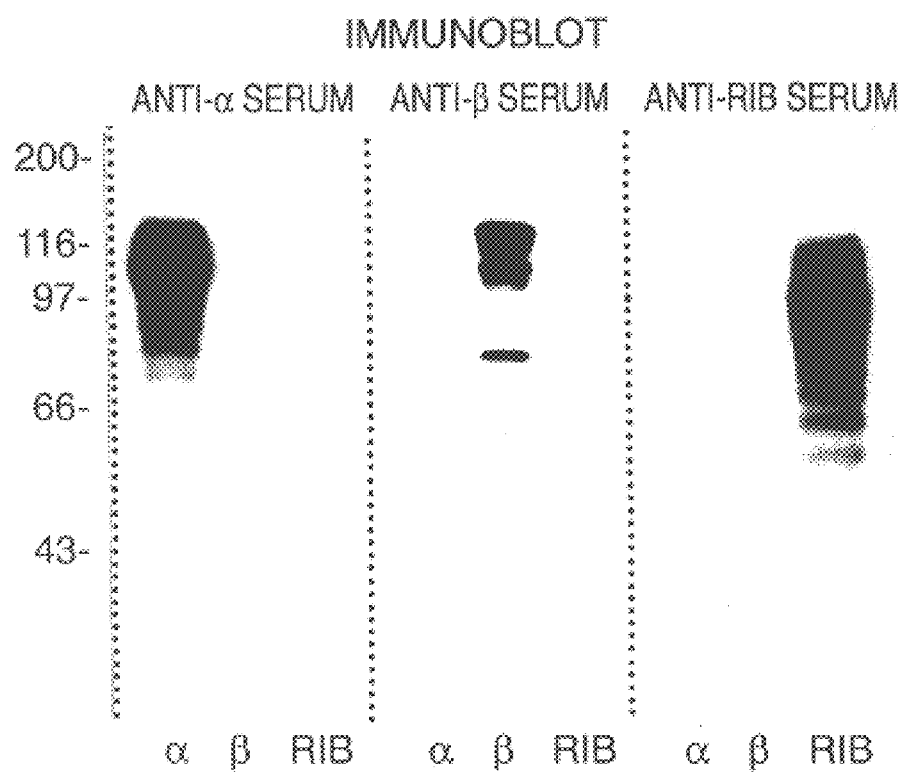

Since protein Rib confers protective immunity, like the alpha and beta proteins, it was of interest to compare these three proteins. A Western blot experiment was performed, using antisera to the purified proteins for the analysis (FIG. 4). The staining gel showed that the three proteins were highly purified, with one major species in each preparation, but there was no serological cross-reaction between the three proteins, as shown in the Western blot.

Figure 5A:
FIGS. 5A, B and C show SDS-PAGE analysis of the purified alpha, beta, and Rib proteins treated with trypsin or pepsin. The trypsin treatment was performed at pH 7.5, the pepsin treatment at pH 4.0. The samples were neutralized before the SDS-PAGE analysis. Controls were treated in the same way as the samples containing trypsin or pepsin, but no enzyme was added; such treatment did not cause degradation of the proteins. P=pepsin; T=trypsin. Molecular mass markers, indicated on the left, are in kD.
Figure 5B:
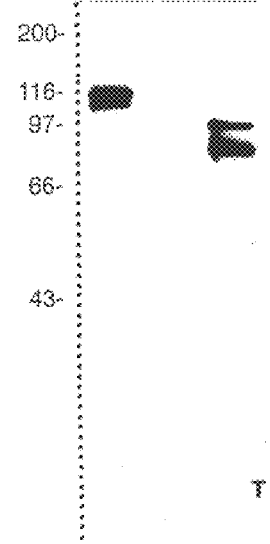
Figure 5C:
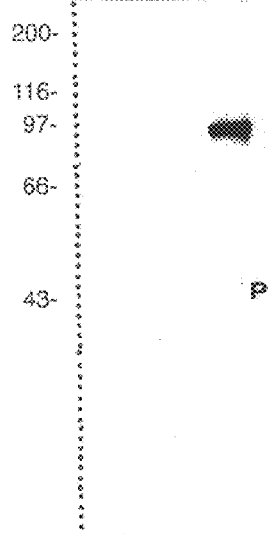

The alpha and beta proteins were originally distinguished due to a difference in protease sensitivity. The alpha protein is resistant to trypsin but sensitive to pepsin, while the beta protein is sensitive to both of these proteases (Bevanger and Maeland, Acta Path Microbiol Scand Sect B 1979. 87:51). An experiment with the purified alpha and beta proteins confirmed this difference and also demonstrated that protein Rib is resistant to both trypsin and pepsin (FIG. 5). As expected, all three proteins were sensitive to degradation by proteinase K (data not shown). The protease resistance of protein Rib was not due to the presence of an inhibitor, since beta protein was completely degraded by both trypsin and pepsin even in the presence of protein Rib (data not shown).

The nucleotide sequence (SEQ ID NO: 3) of the entire rib gene and the deduced amino acid sequence (SEQ ID NO: 4) of the rib protein are shown in FIG. 7. Comparison of this sequence with the NH$_2$-terminal sequence of Rib demonstrated that the signal sequence has a length of 55 amino acid residues. A region with 12 identical repeats (each with a length of 79 amino acid residues (as shown in SEQ ID NO: 6 whose corresponding nucleotide sequence is shown in SEQ ID NO: 5)) and a partial repeat (15 amino acid residues (residues 1–15 of SEQ ID NO: 6)) accounts for >80% of the sequence of the mature protein. As described below, the repeats are apparently identical even at the DNA level. The processed form of protein Rib has a length of 1176 amino acid residues and a predicted molecular mass of 123 kDa.

Initially, a λEMBL3 clone expressing protein Rib was isolated and used to construct the subclone pGRib105 (Example 9). Preliminary sequence analysis of pGRib105 allowed the identification of the 5' and 3' ends of the rib gene. Analysis of the central part of the gene showed that partial digestion with BglII gave rise to a regular ladder pattern on agarose gels, indicating the existence of repeated sequences containing BglII sites. Sequence analysis indeed demonstrated the presence of repeats corresponding to 79 amino acid residues. This initial analysis indicated that Rib has a highly repetitive structure.

Figure 8:
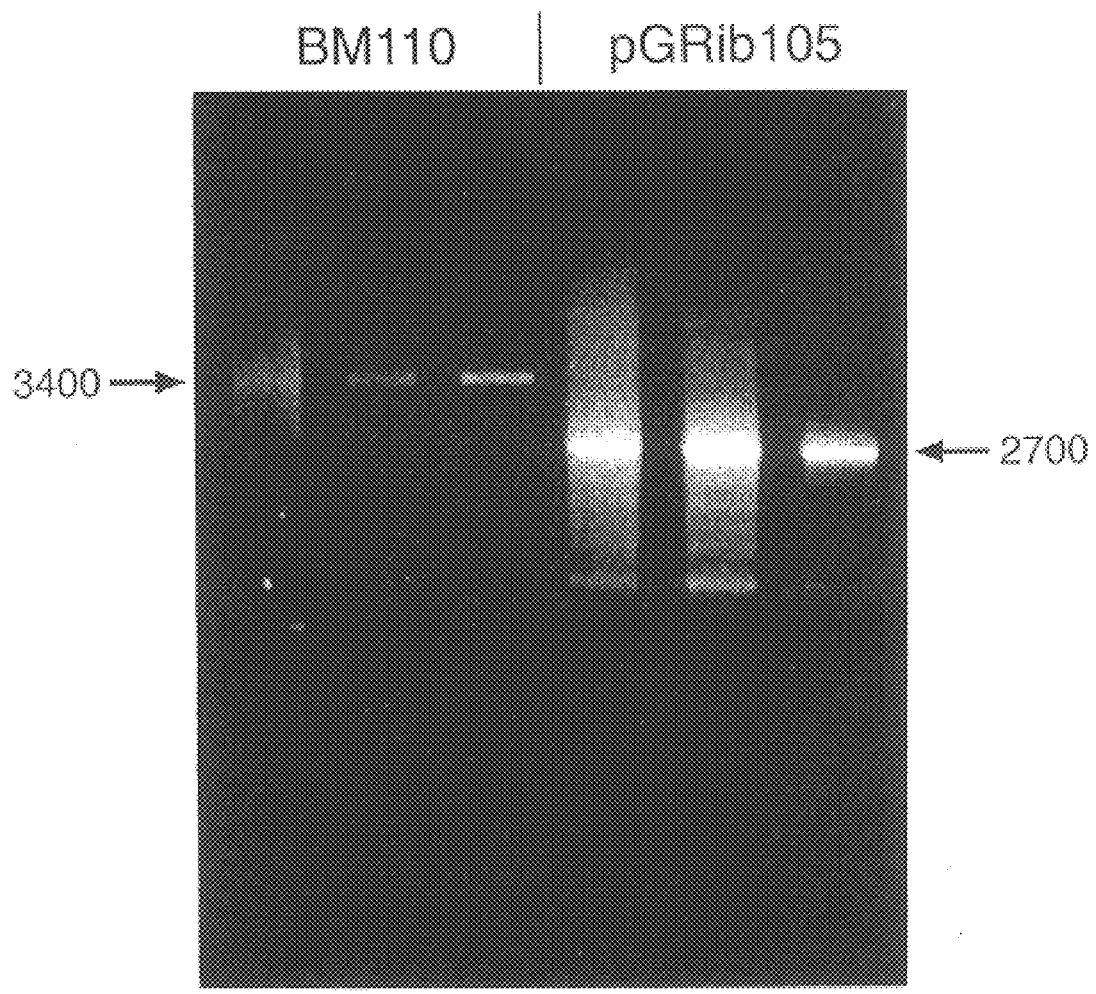
FIG. 8. PCR analysis of the rib gene. PCR products were generated, from streptococcal strain BM110 DNA and from the plasmid clone pGRib105, using fivefold dilutions of the templates. Sizes (in bp) of the main PCR products are indicated. The PCR product of 3,400 bp corresponds to a rib gene with 12 complete repeats and the PCR product of 2,700 bp corresponds to a rib gene with 9 complete repeats.

To further characterize the repeat region, PCR analysis was performed, allowing amplification of the whole rib gene (Example 9). For chromosomal DNA, the main PCR product had a size of ~3,400 bp, corresponding to a rib gene with 12 repeats. However, the pGRib105 subclone generated a main PCR band of ~2,700 bp, corresponding to a rib gene with 9 repeats, implying that part of the repeat region had been lost during the initial cloning in the λ vector. An interesting observation made during the PCR analysis was that the PCR product not only contained the main band but also gave rise to a ladder of bands with a size difference of ~237 bp, corresponding to one repeat (FIG. 8). This ladder could be the result of slippage of Taq polymerase during replication, due to the unique repetitive structure of the rib gene.

Based on the results of the PCR analysis, attempts were made to clone the entire rib gene in E. coli. Since it seemed possible that Rib had a toxic effect on E. coli, the rib gene was cloned without the promoter and signal sequence regions. Appropriate fragments of chromosomal DNA from strain BM110 were cloned directly into the pGEM7Z(f+) vector, generating clone pGRib116. Initial analysis of this clone showed that it contained a repeat region of the same size as the chromosomal rib gene. However, further analysis of pGRib116 indicated that the repeat region in this clone was highly unstable, although it was maintained under Rec⁻ conditions and not expressed. Since the entire repeat region of the rib gene could not be stably maintained in E. coli, it was not possible to analyze the sequence of this region with standard methods.

To analyze the sequence of the repeat region, individual repeats cloned at random were sequenced. As described above, the analysis of the rib gene had indicated that all repeats contained a unique BglII site. Therefore cloned fragments were obtained by BglII digestion of plasmid pGRib116, assuming that they would be representative of the whole repeat region. A total of 13 repeats were analyzed and all of them were found to have identical nucleotide sequences. The conclusion that all repeats are identical was further supported by analysis of sequences at the extremities of the repeat region. The 5' half of the first repeat (up to the BglII site) and the 3' half of the last complete repeat (downstream from the BglII site) together formed a repeat whose nucleotide sequence was identical to that of repeats recovered after BglII digestion. In addition, the partial repeat (coding for 15 amino acid residues) had a nucleotide sequence identical to the corresponding region in the complete repeats.

Comparison between the Rib and α proteins—Previous studies have shown that the α protein of GBS has a very repetitive structure, with long repeats that are identical even at the DNA level (Michel, J. L., Madoff, L. C., Olson, K., Kling, D. E., Kasper, D. L. and Ausubel, F. M., (1992) Proc. Natl. Acad. Sci. U.S.A. 89 10060–10064). As shown in FIG. 9, α protein and Rib protein of GBS exhibit extensive amino acid residue identity. The signal sequences show 80% residue identity and are unusually long: 55 residues in protein Rib (FIG. 7) and 56 residues in the α protein (St alhammar-Carlemalm, M., Stenberg, L. and Lindahl, G. (1993) J. Exp. Med. 177 1593–1603). In the non-repeated $NH_2$-terminal parts of the mature proteins (174 and 170 residues, respectively) the degree of residue identity is 61%. The repeats (79 and 82 residues, respectively) show a somewhat lower degree of residue identity, 47%. The short COOH-terminal regions of the two proteins are almost identical and have the characteristics of cell wall attachment regions in surface proteins of Gram-positive bacteria, including an LPXTG sequence (Schneewind, O., Mihaylova-Petkov, D. and Model, P. (1993) EMBO J. 12 4803–4811).

The Rib and α proteins have an unusually high content of Asp, Val, Thr, Pro, and Lys, which together account for about 60% of the amino acid residues in each protein. Computer assisted analysis indicated that the Rib and α proteins are highly acidic, with isoelectric points of 4.3 and 4.5, respectively. Analysis of the protein sequences by protein structure algorithms (Genetics Computer Group (1994) Program Manual for the GCG Package, Version 8, University of Wisconsin, Madison Wis.; and the GeneWorks program), predicted a high β-sheet content in each protein, including the repeat regions.

Figures 10A, 10B:
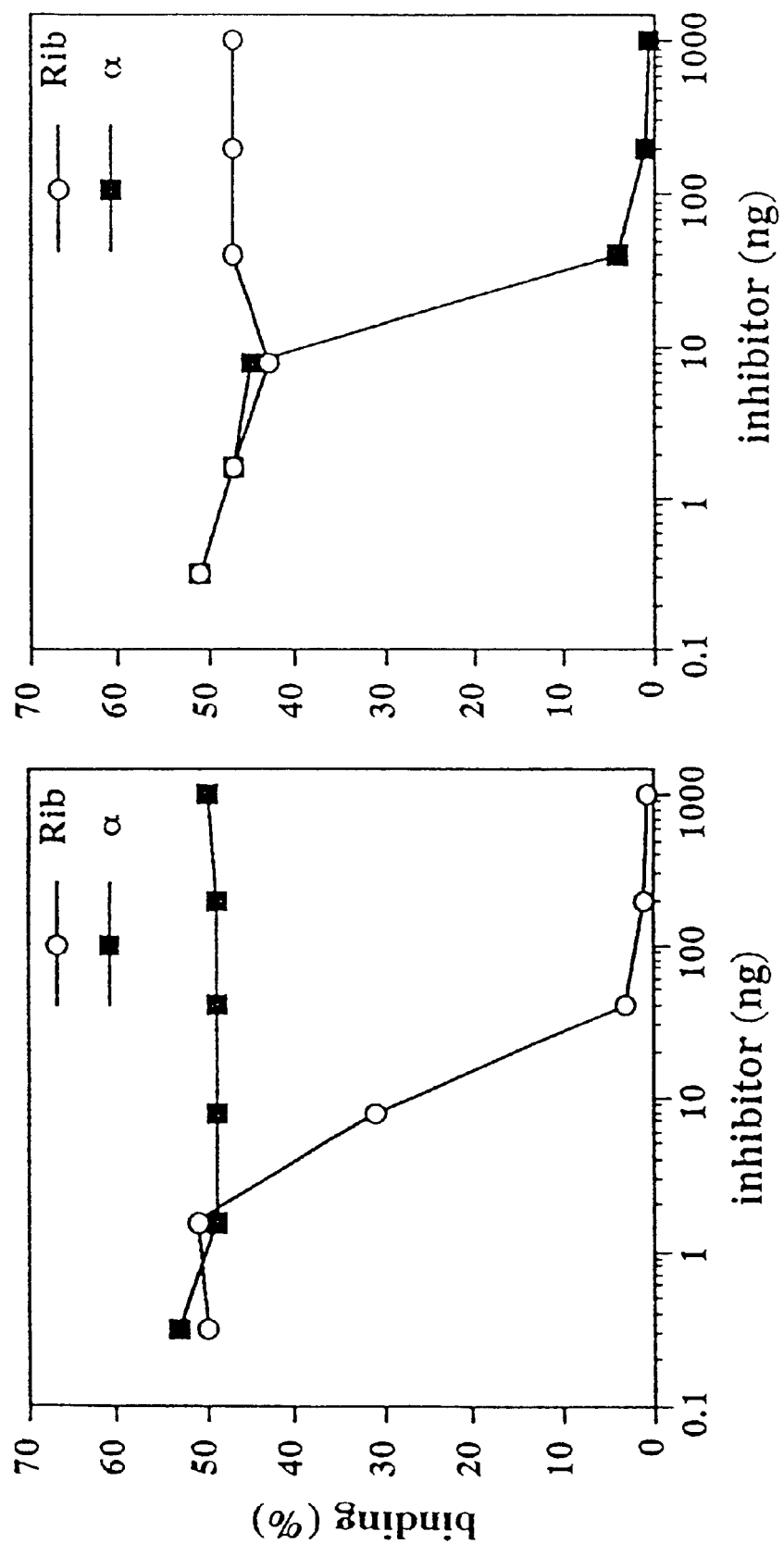
FIGS. 10A and 10B. Immunological relationship between the Rib and α proteins, analyzed by solid phase radioimmunoassay. Highly purified preparations of Rib or α were immobilized in microtiter wells and allowed to react with rabbit antibodies to the corresponding protein. The reactions were inhibited by the addition of increasing amounts of Rib or α.

Immunological relationship between the Rib and α proteins—As indicated above, Rib and α proteins are immunologically unrelated, when analyzed with specific rabbit antisera in Western blots and dot-blots. However, the extensive sequence homology between the two proteins suggested that a crossreactivity might be detected if more sensitive methods were used. To analyze this possibility, inhibition tests were performed (FIG. 10). The reactivity between Rib, immobilized in microtiter plates, and anti-Rib serum was inhibited by pure protein Rib, but addition of the α protein did not cause any inhibition even when a large excess was added (FIG. 10A). Similarly, the reaction between α and anti-α serum was inhibited by purified α protein, but not by protein Rib (FIG. 10B). These results indicate that the large majority of antibodies directed against Rib or α completely lack reactivity for the heterologous antigen.

Figure 11A:
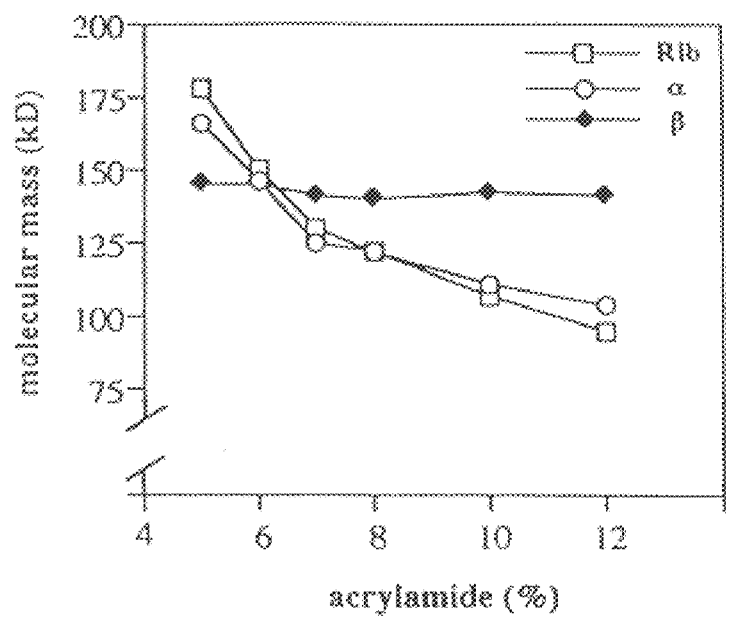
FIGS. 11A–11C. Analysis of the apparent molecular mass of the purified Rib, α, and β proteins.
Figure 11B:
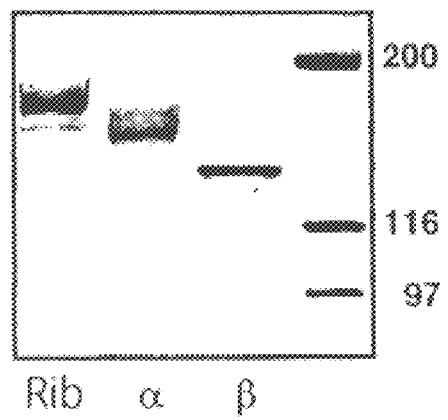
Figure 11C:
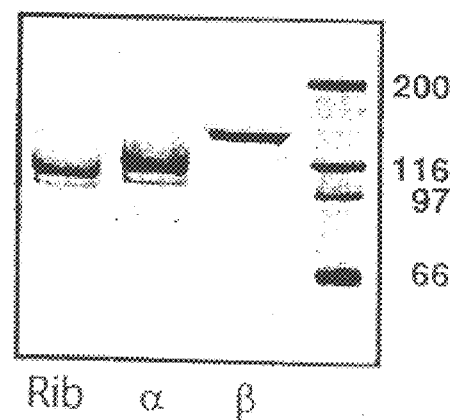

Aberrant migration behaviour of the Rib and α proteins in SDS-PAGE—An unusual feature of Rib and α is their behaviour in SDS-PAGE gels, where the apparent molecular mass of each protein was found to vary depending on the acrylamide concentration of the gel (FIG. 11A). At an acrylamide concentration of 50% the major polypeptide species in the Rib and α protein preparations migrated at positions corresponding to molecular masses of about 178 and 166 kDa, respectively (FIG. 11B), but at an acrylamide concentration of 10% the apparent molecular masses were approximately 107 and 111 kDa, respectively (FIG. 11C). According to the deduced amino acid sequences the predicted molecular masses of the mature Rib and α proteins are 123 and 103 kDa, respectively. Unlike Rib and α, the group B streptococcal β protein, an IgA-binding surface protein that is structurally unrelated to the Rib and α proteins and lacks long repeats (Hédén, L. O. Frithz, E. and Lindahl, G. (1991) Eur. J. Immunol. 21 1481–1490 and Jerlström, P. G. Chhatwal, G. S. and Timmis, K. N. (1991) Mol. Microbiol. 5 843–849), had the same apparent molecular mass in the different SDS-PAGE gels (FIG. 11).

Analysis of ladder patterns generated by the Rib and α proteins in SDS-PAGE : evidence for hydrolysis of acid-labile Asp-Pro bonds—It has previously been reported that bacterial extracts containing the α protein give rise to a regular ladder pattern in immunoblotting experiments, indicating that the α protein is size heterogeneous (Madoff, L. C., Hori, S. Michel, J. L., Baker, C. J. and Kasper, D. L. (1991) Infec. Immun. 59 2638–2644). Interestingly, the distance between the ladder steps was found to correspond to one repeat, suggesting that the different molecular species in the ladder represented polypeptides with different number of repeats (Michel et al. (1992)). A similar ladder pattern was also observed in Western blots of the Rib protein. It may be that this size heterogeneity could be the result of early termination of translation, RNA-mediated self cleavage, acid hydrolysis, or protease activity (Michel et al. (1992)). A repetitive protein from the salivary glands of *Chironomus tentans* has also been shown to form a regular ladder pattern in Western blots, and it was suggested that the heterogeneity reflects a degradation that occurs naturally in the salivary glands (Galli, J. and Weislander, L. (1993) J. Biol. Chem. 268 11888–11893). It was therefore of interest to analyze the mechanism that generates such ladder patterns.

Figure 12A:
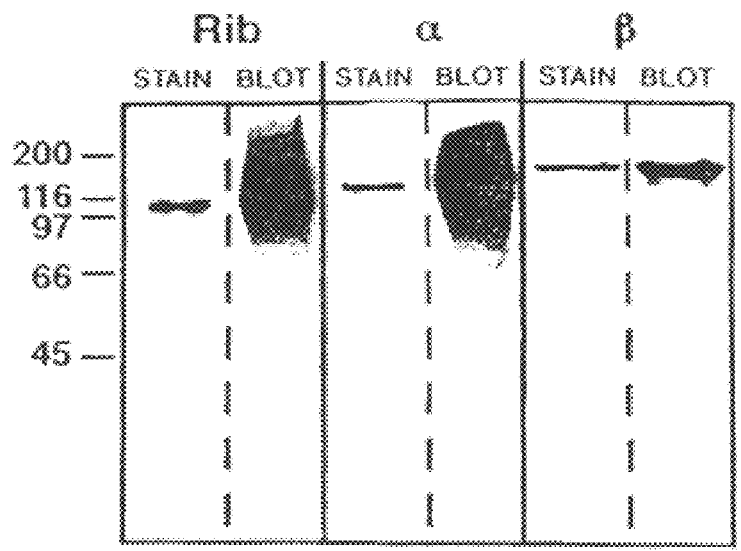
FIGS. 12A–12D. Analysis of ladder patterns formed by the Rib and α proteins in SDS-PAGE.
Figure 12B:
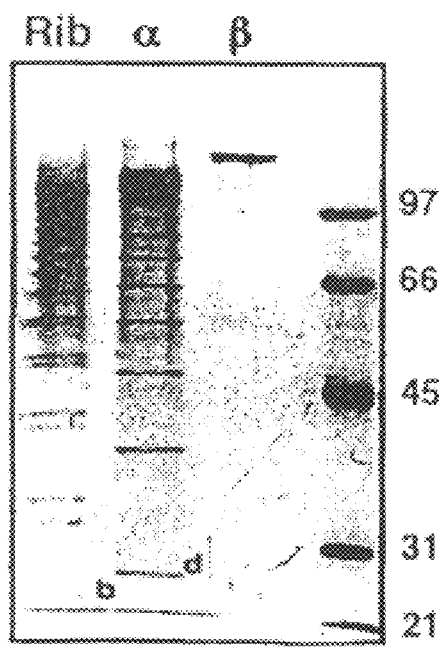
Figure 12C:
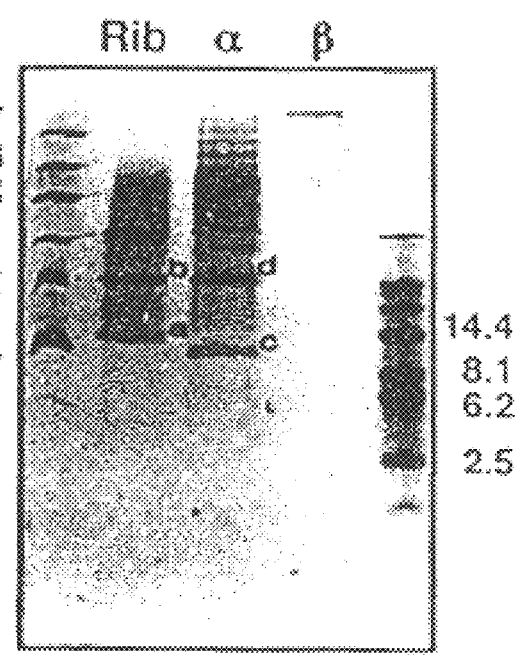
Figure 12D:
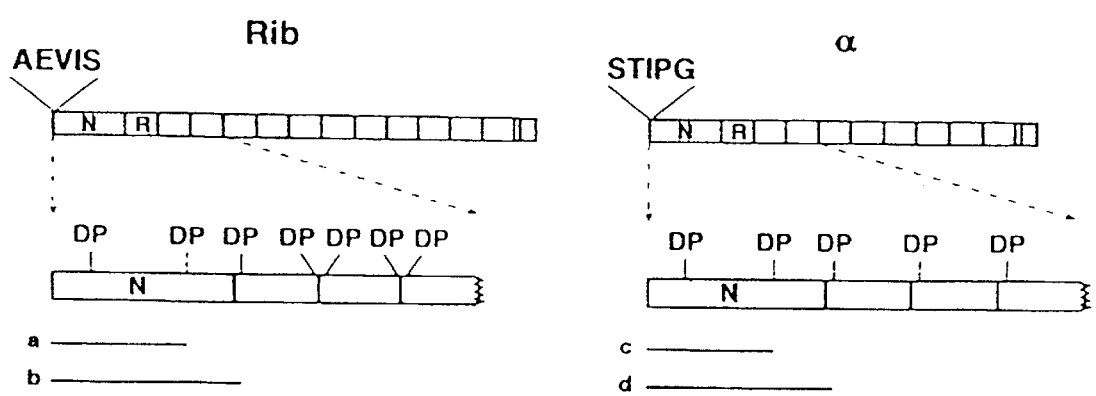

Analysis of the sequences of the Rib and α proteins suggested that the ladder pattern might be due to hydrolysis of Asp-Pro bonds, which are found in the repeats of both proteins (FIG. 12D). It is known that such bonds are sensitive to acid hydrolysis (Landon, M. (1977) Methods Enzymol. 47 145–149). To analyze whether acid-labile sites are responsible for the ladder pattern, purified preparations of the Rib and α proteins were first analyzed under standard conditions (FIG. 12A). Under these conditions, the ladder pattern was seen in blots but not in stained gels, indicating that only a small fraction of the purified proteins were of lower molecular weight and gave rise to the ladder (FIG. 12A). Next, the purified Rib and α proteins were incubated at pH 4.0 at 37° C. for 16 h before analysis. The resulting preparations were either boiled directly in sample buffer or neutralized before boiling in sample buffer. When these preparations were analyzed by SDS-PAGE, the analysis showed that distinct ladder patterns, readily detectable also in stained gels, were formed when the proteins has been boiled for 5 min in sample buffer at acidic pH (FIG. 12B). However, only a minor degradation was detected in the samples that had been neutralized-before the analysis (data not shown). Thus, the ladder patterns were largely due to fragmentation during boiling in non-neutralized sample buffer (FIG. 12B). The Rib and α proteins were further degraded when the samples were boiled at acidic pH for a longer period (15 min), as detected in a stained tricine gel (FIG. 12C). In contrast, the group B streptococcal β protein, which does not contain Asp-Pro sequences, was not degraded at acidic pH (FIGS. 12B and 12C). The repeats in the Rib protein contain two Asp-Pro sites (FIG. 12D) which may explain why this protein gives rise to doublet bands (FIG. 12B).

To further analyze the formation of the ladder, bands generated by the Rib and α proteins at acidic pH were subjected to $NH_2$-terminal sequence analysis. Bands analyzed included those labeled a–d in FIGS. 12B and 12C, as well as polypeptides of higher molecular weight. All bands analyzed had sequences identical to the $NH_2$-terminal sequences of the mature proteins, i.e., AEVIS for the Rib protein and STIPG for the α protein (FIG. 12D). These data may be explained by assuming that acid hydrolysis occurred at all Asp-Pro sites in the Rib and α proteins, except the most $NH_2$-terminally located site in each protein, which would have given rise to a short $NH_2$-terminal fragment that was not detected.

Although the data reported above suggest that the ladder pattern observed for the Rib and α proteins is generated by cleavage of Asp-Pro bonds, cleavage of such bonds would be expected to generate both NH$_2$-terminal and COOH-terminal fragments as well as internal peptides generated by hydrolysis of Asp-Pro sites in the repeats (7.2 and 1 kDa peptides from the repeats of protein Rib and an 8.7 kDa peptide from the repeats of the α protein). Surprisingly, neither COOH-terminal fragments nor internal peptides were found, indicating that these peptides had been further degraded or lost during the analysis (FIG. 12C). Interestingly, the ladder pattern formed by the salivary gland protein from C. tentans also showed the absence of internal peptides corresponding to single repeats (Galli, J. (1993)).

The invention will now be described with the following examples, which however do not limit the scope of the invention.

EXAMPLE 1

Identification of the Protein

Four group B streptococcal strains representing the four main serotypes were used as reference strains: A909, type Ia/c; SB35, type Ib; B1284, type II; BS30, type III, described here. The BS30 strain was isolated at Lund University Hospital from a boy with neonatal infection. All bacterial strains were grown in Todd-Hewitt broth (Oxoid) at 37° C., without shaking. Mutanolysin extracts of the strains were analyzed by SDS-PAGE and by immunoblotting using antisera to the alpha and beta proteins. Small-scale mutanolysin extracts of streptococcal strains were prepared as described for the large-scale extracts used for protein purification, but cultures of only 50 ml were used to prepare 20% bacterial suspensions, of which 1 ml samples were digested with the enzyme.

SDS-PAGE was performed with standard techniques, using a total polyacrylamide concentration of 10% and a cross-linking of 3.3%. Samples were boiled for 3 min in a solution containing 2% SDS and 5% 2-mercaptoethanol prior to electrophoresis. The separated proteins were stained with Coomassie Brilliant Blue R-250 or transferred by electroblotting to a membrane of methanol-activated polyvinylidene difluoride (Immobilon-P; Millipore Corp., Molsheim, France), using a Semi-Dry Electroblotter (Ancos, Vig, Denmark). The Immobilon membranes were blocked with gelatin, using standard procedures, and then incubated with the indicated type of rabbit antiserum diluted 1000-fold (see example 7), followed by radiolabelled protein G and autoradiography.

Proteins were radiolabelled with carrier-free $^{125}$I (Amersham International, England), using the chloramine T method. Total protein concentrations were determined with the MicroBCA protein assay reagent (Pierce). Electroelution of protein from SDS-PAGE gels was performed with a model 422 Electro-Eluter from Bio-Rad.

The results are shown in FIG. 1.

EXAMPLE 2

Purification of Protein Rib

The bacteria in a 10 l overnight culture of strain BS30 were spun down, washed twice with 50 mM Tris, pH 7.3, and resuspended to 20% (v/v) in the same buffer. Mutanolysin (Sigma Chemical Co., St. Louis, Mo.), dissolved to 5000 units/ml in 10 mM potassium phosphate, pH 6.2, was then added to the bacterial suspension (125 ml) to give a final concentration of 350 units/ml. The digestion was allowed to proceed for 17 h at 37° C. with gentle shaking, and protease inhibitors were then added to the following final concentrations: benzamidine chloride, 5 mM; iodoacetic acid, 5 mM; phenylmethyl sulfonyl fluoride, 2 mM. The suspension was centrifuged and the supernatant was immediately dialyzed (dialysis tubing Spectrapor No. 4) against 10 mM Tris, pH 8.0. This dialyzed preparation was subjected to two consecutive steps of ion exchange chromatography, which allowed the best recovery of pure protein Rib, as shown by preliminary experiments. The presence of protein Rib was analyzed by SDS-PAGE and visual inspection of the gels for the presence of the 95-kD band. In the first chromatography step, the dialyzed preparation (110 ml) was mixed with the same volume of 0.4 M NaCl in 10 mM Tris, pH 8.0 and 30 ml of DEAE Bio-Gel A (BioRad Laboratories, Richmond, Calif.), equilibrated with 10 mM Tris, pH 8.0. This mixture was stirred gently at 4° C. for 1 h, and unabsorbed material (containing protein Rib) was freed from the gel by filtration through a glass filter. For the second chromatography step (FIG. 2A), the filtrate containing protein Rib was diluted twenty-fold with distilled water, to reduce the ionic strength, and mixed with 30 ml of DEAE Bio-Gel A, equilibrated as described above. After gentle stirring at 4° C. for 16 h, the gel was recovered by filtration and washed with 10 mM Tris, pH 8.0. Absorbed proteins (including protein Rib) were eluted with an 800 ml linear salt gradient (0–0.2 M NaCl in 10 mM Tris, pH 8.0), followed by 1 M NaCl (60 ml). Fractions (10 ml) were collected and those containing protein Rib were pooled, concentrated, and subjected to gel filtration in a column of Sepharose CL6B (4.2 cm×90 cm) in PBSA (0.12 M NaCl, 0.03 M phosphate, 0.02% NaN$_3$, pH 7.2) (FIG. 2B). The fractions were analyzed by SDS-PAGE electrophoresis for presence of the 95-kD band. Fractions (10 ml) containing protein Rib were pooled and frozen. The yield of protein Rib was about 6 mg from 25 g of bacteria. To ensure the purity of the protein Rib preparations used for immunochemical analysis, the protein used for such work was further purified by SDS-PAGE, followed by electroelution of the 95-kD band. However, SDS-PAGE analysis did not demonstrate any difference in purity between this electro-eluted material and that recovered from the gel filtration step.

As mentioned above, protein Rib is also found in the medium of strains expressing the protein. The protein can be purified from such a medium, using techniques similar to those described above.

Automated amino acid sequence analysis of protein bands transferred to Immobilon was performed directly on the membranes, using an Applied Biosystems 470A gas-liquid solid-phase sequenator. The membranes were lightly stained with Coomassie Brilliant Blue to localize the protein bands, which were then cut out for sequencing. The SwissProt Data Bank was used for analysis of protein sequences.

The NH$_2$-terminal sequence of protein Rib from strain BS30 is shown in SEQ ID NO:1. The two proteins with estimated molecular masses of 95 kD and 90 kD in purified protein Rib (FIG. 2B) were found to have the same NH$_2$-terminal sequence, suggesting that the smaller molecule is a degradation product of the larger one. A data search showed that the NH$_2$-terminal sequence of protein Rib is unique.

The same purification procedure was also followed for the isolation of protein Rib from strain BM110. The NH$_2$-terminal sequence (SEQ ID NO:2) of protein Rib isolated from strain BM110 may differ from the NH$_2$-terminal sequence of the corresponding protein from BS30 at position 7, where the BM110 protein may have Ser in place of Asp.

EXAMPLE 3

Purification of the Alpha Protein

The alpha protein was purified from strain SB35, a type Ib strain expressing both the alpha and beta proteins. The procedure used was similar to that used for purification of protein Rib from strain BS30. Fractions were analyzed for the presence of alpha protein by dot-blot analysis, using rabbit anti-alpha serum (kindly provided by Dr. L. Bevanger, University of Trondheim, Norway) and protein G (Calbiochem Co., San Diego, Calif.) radiolabelled with $^{125}$I. In the ion exchange and gel filtration steps, the behaviour of the alpha protein was similar to that of protein Rib (cf. FIG. 2). The alpha protein recovered from the gel filtration step was present in a sharp peak. Analysis of this material with different antisera indicated that it contained trace amounts of contaminating beta protein, which was removed by passage of the preparation through a small column of IgA-Sepharose. The purified alpha protein had a molecular weight of about 110,000, according to SDS-PAGE analysis (cf. FIG. 4). The yield of alpha protein was 12 mg from 39 g of bacteria. The alpha protein used for immunochemical work was further purified by electroelution from SDS-PAGE gels, as described above for protein Rib. However, SDS-PAGE analysis did not demonstrate any difference in purity between this electro-eluted material and that recovered from the gel filtration step.

EXAMPLE 4

Purification of the Beta Protein

The IgA-binding beta protein (Russell-Jones et al, *J Exp Med* 1984. 160: 1467) was purified by a procedure similar to that used for the Rib and alpha proteins. The starting material was obtained by incubating washed SB35 bacteria in 50 mM glycine-NaOH buffer, pH 11.0 (final pH in suspension 9.7). Previous work in our laboratory had shown that the major protein species in such an extract is the beta protein. The extract (222 ml) was immediately dialyzed against 10 mM Tris, pH 8.0, diluted twenty-fold with distilled water and mixed with 40 ml of DEAE Bio-Gel A (equilibrated with 10 mM Tris, pH 8.0). After gentle stirring at 4° C. for 2 h, the gel was transferred to a column and eluted with an 800 ml linear salt gradient (0–0.2 M NaCl in 10 mM Tris, pH 8.0). A dot blot procedure was used to test fractions (10 ml) for presence of beta protein, using radiolabelled IgA or anti-beta serum and radiolabelled protein G for the analysis. The beta protein was eluted in the first part of the gradient. Appropriate fractions were pooled, concentrated, and subjected to gel filtration on a column (4.2×100 cm) of AcA34 (Pharmacia-LKB, Uppsala, Sweden) in PBSA. The beta protein was eluted in a well-defined peak. Appropriate fractions were pooled, concentrated and frozen. The yield was 9 mg of pure protein from 23 g of bacteria. The major protein species in such a preparation had a molecular weight of about 130,000, according to SDS-PAGE, but small amounts of degradation products of lower molecular weight were also seen when the protein was subjected to Western blot analysis.

EXAMPLE 5

Analysis of Protease Sensitivity

For analysis of protease sensitivity (FIG. 5), 200 µl samples of purified alpha, beta or Rib protein (0.5 mg/ml) were incubated for 1 h at 37° C. with trypsin, pepsin, or proteinase K (0.2 mg/ml). Trypsin digestion was performed in 0.25 M sodium phosphate, pH 7.5, pepsin digestion in 0.25 M sodium acetate, pH 4.0, and proteinase K digestion in 0.25 M Tris, pH 7.4. The samples were neutralized before analysis by SDS-PAGE.

EXAMPLE 6

Analysis of Streptococcal Strains for Cell Surface Expression of the Alpha, Beta and Rib Proteins Five reference strains available in our laboratory were first analyzed for surface expression of the alpha, beta and Rib proteins. Later, a collection of 58 group B streptococcal strains, all isolated from cases of invasive infections, were also used to study the expression of these cell surface proteins (see Table 1). Typing of group B streptococcal strains was performed in the Clinical Microbiology Laboratory of Lund University Hospital, using standard techniques.

The bacteria in a 10 ml overnight culture were washed twice with PBSAT (PBSA supplemented with 0.05% Tween 20) and a 1% suspension in PBSAT was prepared. A sample (180 µl) of this bacterial suspension was mixed with 20 µl of rabbit antiserum that had been diluted in PBSAT and the mixture was incubated at 23° C. for 1 h. Two ml of PBSAT were then added, the bacteria were spun down, washed once with 2 ml of PBSAT, and resuspended in 200 µl of PBSAT. For detection of bound IgG, 25 µl of radiolabelled protein G (about $10^4$ cpm in PBSAT) was then added and incubation was continued at 23° C. for 1 h. Following addition of 2 ml of PBSAT, the bacteria were spun down and the pellet was then washed by addition of 2 ml of PBSAT. After a final centrifugation, the supernatant was discharged and the radioactivity in the pellet was determined. When many strains were tested for expression of the alpha, beta and Rib proteins (Table 1), a single final antiserum dilution of 1:1,000 was used. Controls with preimmune rabbit antiserum were always included and were completely negative in all cases. Protein Rib was found on the cell surface of 31 out of 33 type III strains, but not on any of the 12 strains of types Ia and Ib.

TABLE 1

Cell surface expression of the alpha, beta and Rib proteins by 58 group B streptococcal strains isolated from patients with invasive infections *

| Protein expressed | Ia (n = 9) | Capsular type Ib (n = 3) | II (n = 13) | III (n = 33) |
|---|---|---|---|---|
| alpha | 6 | 0 | 4 | 0 |
| beta | 1 | 0 | 0 | 0 |
| alpha and beta | 1 | 3 | 5 | 0 |
| Rib | 0 | 0 | 1 | 31 |
| none | 1 | 0 | 3 | 2 |

The cell surface expression of the alpha, beta, and Rib proteins was analyzed with specific antisera, and bound antibodies were detected with radiolabelled protein G, as shown in FIG. 3.

The 58 strains studied here were all isolated from cases of invasive infections, but do not represent a random collection of such strains, since most of the type II strains were later added to the collection originally studied, which included only two type II strains.

EXAMPLE 7

Preparation of Antisera and Mouse Protection Tests

All antisera were produced in rabbits, which were immunized s.c. on the back. For preparation of antiserum to protein Rib expressed by strain BS30, slices corresponding to several 95 kD bands in SDS-PAGE gels were cut out, divided into small pieces and mixed with complete Freund's adjuvant. For the initial immunization, six slices (about 60 µg of protein) in 1 ml of PBS were mixed with 1 ml of adjuvant. Three bands (30 µg of protein) were used for booster injections. The first booster was given after 4 weeks and 3 additional boosters were given with intervals of 2 weeks. The rabbit was then bled 3 times with intervals of 3 weeks; the serum obtained from these 3 bleedings was pooled and used for the experiments reported here. Antiserum to the alpha protein was prepared by the same procedure. The first sample of anti-alpha serum, used to analyze fractions during the purification, was obtained from Dr Lars Bevanger, Trondheim. Antiserum to the purified beta protein was available in our laboratory.

C3H/HeN mice, bred in our department, were used at an age of 10–20 weeks. The mice were injected i.p. with 0.5 ml of a rabbit serum diluted five-fold in PBS, and infected 4 h later by i.p. injection of 0.5 ml of log-phase bacteria diluted in Todd-Hewitt broth. The number of bacteria used, which was estimated to be the 90% lethal dose ($LD_{90}$), was $2 \times 10^6$ c.f.u. for strains BM110, BE210, and SB35sed1, and $2 \times 10^7$ c.f.u. for BS30 and L25. Dead animals were counted daily for 4 days. Control animals usually died within 24 h.

TABLE 2

Rabbit antiserum to protein Rib protects mice against lethal infection with group B streptococcal strains expressing this protein

| Strain | Capsular type | Relevant cell surface protein* | Mice surviving† after pretreatment with | | |
|---|---|---|---|---|---|
| | | | anti-Rib serum | anti-alpha serum | normal serum |
| BS30 | III | Rib | 29/32§ | 1/15 | 4/20 |
| BM110 | III | Rib | 15/24§ | 0/15 | 0/15 |
| L25 | III | — | 0/15 | 2/14 | n.d.‖ |
| BE210 | II | Rib | 10/15¶ | 0/14 | n.d. |
| SB35 sed 1 | Ib | alpha | 1/15 | 10/15** | n.d. |

C3H/HeN mice were injected i.p. with 0.1 ml of rabbit antiserum (diluted to 0.5 ml with PBS) and challenged 4 h later with an $LD_{90}$ dose of log-phase bacteria, diluted into 0.5 ml of Todd-Hewitt broth. The survival data were analyzed by the chi-square test.
*Expression of protein Rib or the alpha protein, the two antigens relevant to these experiments
†No. of mice surviving for 4 days/total no. of infected mice
§$P < 0.001$ when compared to the controls receiving anti-alpha serum or normal serum
‖n.d. = not determinated
¶$P < 0.001$ when compared to the controls receiving anti-alpha serum
**$P < 0.01$ when compared to the controls receiving anti-Rib serum The data in Table 2 demonstrate that antiserum to protein Rib protects against lethal infection with BS30, the type III strain from which the protein had been purified. This protection is not unspecific, as shown by the experiments with control sera. The anti-Rib serum also protected against lethal infection with another type III strain, BM110, a member of the high-virulence clone of group B streptococcal strains (Musser et al., *Proc. Natl. Acad. Sci* USA 1989. 86: 4731) In contrast, the anti-Rib serum did not protect against infection with L25, one of the type III strains that do not express protein Rib (Table 1). The protective effect of anti-Rib serum was not limited to type III strains, as shown by the experiments with a type II strain expressing protein Rib. As expected, anti-Rib serum did not protect against a type Ib strain expressing the alpha antigen. Taken together, these data strongly suggest that protein Rib acts as a virulence factor in almost all type III strains and in some type II strains, i.e., in most group B streptococcal strains causing invasive infections.

EXAMPLE 8

Cloning of the rib-Gene and Expression of Protein Rib in *Escherichia coli*

Figure 6A:
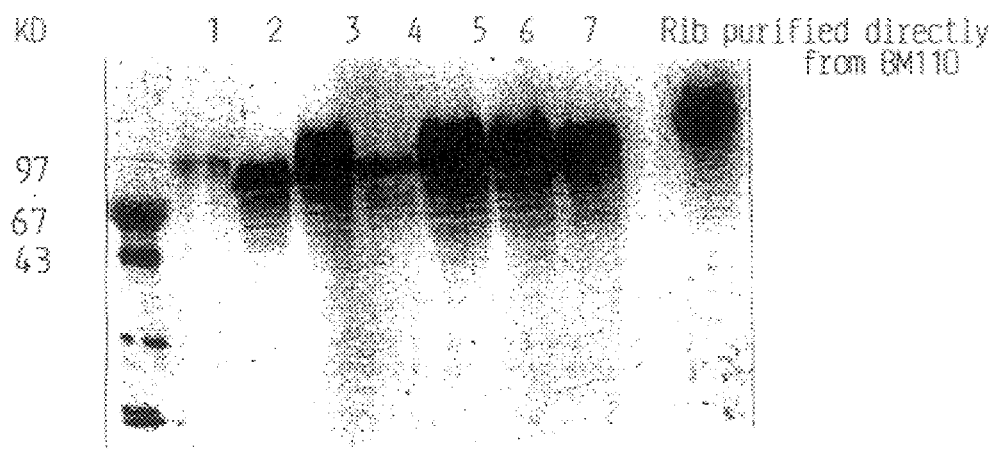
FIGS. 6A, 6B and 6C show the results of cloning of the rib-gene from strain BM110 and expression of protein Rib in *Escherichia coli*. (A) Western blot analysis of 7 different 1 clones. Incubation with anti-Rib. (B) Restriction digests of chromosomal DNA from strain BM110. (C) Restriction digests of the Rib expressing 1-clone 1rib3.
Figure 6B:
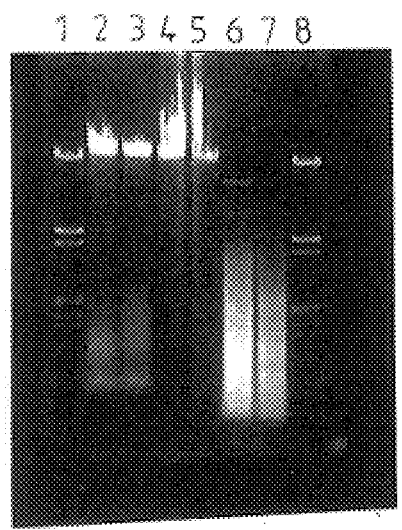
Figure 6C:
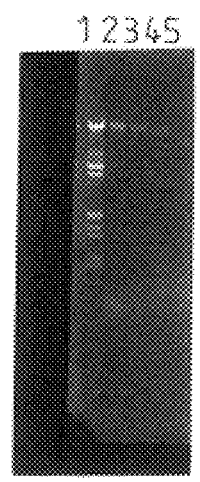

The structural gene for protein Rib was cloned from strain BM110, a serotype III strain which is a member of a high-virulence clone. Protein Rib expressed by this strain (SEQ ID NO:2) and protein Rib expressed by strain BS30 (SEQ ID NO:1) have similar size and $NH_2$-terminal sequence. A library of strain BM110 DNA in bacteriophage lambda was constructed. The bacteria in a 500 ml log-phase Todd-Hewitt culture of the strain BM110 were spun down. The pellet was frozen and thawed 3 times, suspended in 20 ml TE buffer (10 mM Tris, 1 mM EDTA pH 8.0), centrifugated, washed and resuspended in 4 ml of the same buffer. Mutanolysin (Sigma Chemical Co. St Louis, Mo., USA) dissolved to 5000 units/ml in 10 mM potassium phosphate, pH 6.2, was added to the bacterial suspension to give a final concentration of 500 units/ml. Lysozyme (Sigma) was added to a final concentration of 8 mg/ml, and the digestion was allowed to proceed for 3 h at 37° C. The bacterial cells were lysed by addition of 200 ml of 10% SDS and 500 ml Tween lysing mix (2% Tween-20, 50 mM Tris pH 8.0 and 60 mM EDTA), followed by another 200 ml of 10% SDS. The lysate was treated with proteinase K (Sigma, 100 mg/ml) for 19 h at 50° C., followed by repeated phenol and chloroform extractions. The DNA was precipitated with ethanol, dried in a SpeedVac concentrator (SAVAC) and dissolved in 4.5 ml TE buffer. The DNA was further purified by CsCl density gradient ultracentrifugation and dialysed against TE buffer. The DNA concentration was then approximately 2.5 mg/ml. This DNA was partially digested with Sau 3AI (Promega), and ligated to Bam HI-cleaved arms of lEMBL 3 (Statagene). The recombinant phage DNA was packaged in vitro using Gigapack II Gold Packaging Extract (Stratagene). The library was plated on the *E. coli* strain LE392 and screened for production of protein Rib with an immuno-blotting technique: plates with about 1000 plaques were covered with a nitrocellulosa membrane and left at 4° C. for 1 h. The membranes were removed, blocked, and incubated in buffer containing rabbit anti-Rib serum, diluted 50-fold. Positive plaques, i.e., those binding rabbit IgG, were detected by addition of peroxidase-labeled protein A (Sigma) (20 mg/ml) and the presence of peroxidase was visualized, using standard techniques. Seven independent Rib expressing lambda clones were isolated. Three of these clones, i.e., lambda Rib1-3, lambda Rib1-5 and lambda Rib1-7, were deposited at Deutsche Sammlung von Microorganismen with deposit numbers DSM 9039, DSM 9040 and DSM 9041 respectively. A preparation of DNA from the lambda Rib1-3 clone having a DNA concentration of about 0.5 mg/ml was also made. Lysates of these seven clones were subjected to Western immunoblot analysis, using anti-Rib serum (see FIG. 6). Several of the clones express protein Rib of the same size as protein Rib isolated directly from strain BM110.

EXAMPLE 9

Isolated and Sequencing of the Rib Protein

Bacterial Strains and Cloning Vectors—The GBS strain BM110 is a serotype III isolate obtained from Dr. S. Mattingly (University of Texas, San Antonio, Tex.) as described above. *Escherichia coli* strain LE 392 (Genofit, Geneva, Switzerland) was used as a host for the cloning vector λEMBL3 (Promega Co., Madison, Wis.). For subcloning, *E. coli* strain XL1-Blue (which is recA1) (Stratagene, La Jolla, Calif.) was used as a host for the cloning vector pGEM7Z (f+) (Promega Co.), and the *E. coli* strain JM103 (Amersham Corp.) was used as a host for the sequencing vectors M13mp18 or M13mp19 (Amersham Corp.). Standard techniques were used for work with *E. coli* and cloning vectors (Sambrook, J., Fritscn, E. F. and Maniatis, T. (1989) Molecular Cloning: A Laboratory Manual, 2nd Ed., Cold Spring Harbor Laboratory Press, Cold spring Harbor, N.Y.).

Media, Chemicals, and Purified Proteins—GBS was grown in Todd-Hewitt broth, and *E. coli* was grown in LB broth at 37° C. Ampicillin (50 µg/ml) and tetracycline (5 µg/ml) were added when appropriate. Restriction enzymes were purchased from Promega Co., New England Biolabs Inc. (Beverly, Mass.) or Boehringer Mannheim.

The Rib, α, and β proteins were purified from extracts of strains BM110, A909, and SB35, respectively, by a combination of ion exchange and molecular sieve chromatography as described above and in Stålhammer-Carlemalm et al. (1993), followed by a final step of hydroxylapatite chromatography for removal of small amounts of contaminating polysaccharides.

DNA Sequencing and Sequence Analysis—DNA sequences were determined by the dideoxy chain termination method using [α-$^{35}$S] dATP (Amersham Corp.) and Sequenase 2.0 (Amersham Corp.). Recombinant M13amp18 or M13mp19 phage DNA was used as template. M13 universal primer and −40 primer (Amersham Corp.) as well as custom made primers were used. The sequencing reaction products were resolved on 8% polyacrylamide-urea gels. Gels were run at 40 W for 1–4 h on a sequencing unit from Cambridge Electrophoresis Ltd. (Cambridge, UK), fixed in 10% methanol, 10% acetic acid for 15 min, and dried on Watman 3MM papers under vacuum. Computer-assisted analysis of DNA sequences was performed with the GCG software package (Genetics Computer Group (1994)) and the GeneWorks program (IntelliGenetics, Inc., Mountain View, Calif.).

Polymerase Chain Reaction Analysis—The rib gene was amplified from purified DNA in a 50-µl volume using primers with the sequences 5'-TGACTAAAAATGTTCAGAATGGTAG-3' (SEQ ID NO: 7) and 5'-GAAACAGATAATAAACCAACTGATG-3' (SEQ ID NO: 8). Each reaction mixture contained 12.5 pmol of each primer, 0.2 mM dNTPs, 2.5 units AmpliTaq DAN polymerase (Perkin-Elmer) and 1.5 MM MgCl$_2$ in the incubation buffer supplied with the enzyme. PCR amplification was performed by 30 repeated cycles on a programmable thermal controller (PTC-100, Promega Co.) with a thermal step program that included: denaturation at 94° C. for 60 s, annealing at 57° C. for 60 s, and primer extension at 72° C. for 120 s. Amplified material was analyzed on 1.0% agarose gels.

Solid Phase Radioimmunoassay—Microtiter plates (Falcon 3912, Becton Dickinson, Oxnard, Calif.) were coated with purified protein Rib or α by incubation for 16 h with 100 µl of a solution (100 ng/ml) of protein in PBS (0.03 M phosphate, 0.12 M NaCl, pH 7.2). The wells were blocked by washing with VBS (10 mM veronal buffer, 0.15 M NaCl, pH 7.4) supplemented with 0.25% gelatin and 0.25% Tween 20. Rabbit antisera against the Rib and α proteins, obtained as indicated above, were used at dilutions corresponding to 50–60% of maximal binding. The binding between anti-Rib and immobilized Rib, and between anti-α and immobilized α, was inhibited by the addition of purified Rib or α. For these inhibition experiments 100 µl aliquots of antiserum in PBSAT (PBS containing 0.02% NaN$_3$ and 0.05% Tween20) were preincubated for 30 min with various amounts (160 pg to 500 ng) of Rib or α and then added to the wells. After 3 h of incubation the wells were washed three times with PBSAT and the presence of antibodies was analyzed by addition of $^{125}$I-labeled protein G (20,000 cpm in 100 µl/well) and incubation for 2 h. After three washes with PBSAT, the radioactivity of each well was determined in a γ-counter. Non-specific binding (less than 1%) was determined in wells coated with buffer (PBS) alone. All incubations were performed at room temperature. Other methods—SDS-PAGE was performed using a Protean II cell (Bio-Rad, Hercules, Calif.). The gels were stained with Coomassie brilliant blue R-250 or transferred by electroblotting to Immobilon filters (Millipore Corp., Molsheim, France) in a Semi-Dry Electroblotter (Ancos, Vig, Denmark). Tricine gels were used for the analysis of peptide fragments (Sch agger, H. and von Jagow, G. (1987) Anal. Biochem. 166 368–379). For Western blot analysis, membranes were incubated with antisera as described. Amino-terminal sequence analysis of proteins transferred to ProBlott membranes was performed with a 470A Protein Sequencer (Applied Biosystems, Foster City, Calif.).

EXAMPLE 10

Kit

The components of the present invention may be packaged as a kit. Uses of the kit may be for the detection of antibodies to protein Rib or for the detection of protein Rib, however other uses are possible. Each component of the kit(s) may be individually packaged in its own suitable container. The individual containers may also be labelled in a manner which identifies the contents. Moreover, the individually packaged components may be placed in a larger container capable of holding all desired components. Associated with the kit may be instructions which explain how to use the kit. These instructions may be written on or attached to the kit.

What is claimed is:

1. An isolated DNA comprising one or more repeats of SEQ ID NO:5, wherein the isolated DNA is not group B streptococcus chromosomal DNA.

2. An isolated DNA comprising one or more repeats encoding the polypeptide of SEQ ID NO:6.

3. An isolated DNA comprising a nucleotide sequence which encodes the polypeptide of SEQ ID NO:4.

4. The isolated DNA of claim 3, comprising the open reading frame of SEQ ID NO:3.

5. A vector comprising the isolated DNA of any one of claims 1, 2, 3 and 4.

6. A non-human host cell comprising the vector of claim 5.

7. A composition comprising, isolated DNA comprising a sequence selected from the group consisting of:
   i) one or more repeats of SEQ ID NO:5, and
   ii) a nucleotide sequence which encodes the polypeptide of SEQ ID NO:4,
   wherein said isolated DNA is not chromosomal DNA, and a suitable pharmaceutically acceptable carrier.

* * * * *